United States Patent [19]

Howatt

[11] 4,176,396

[45] Nov. 27, 1979

[54] APPARATUS FOR DIRECTLY MEASURING MACHINE TOOL WEAR

[75] Inventor: John R. Howatt, Waltham, Mass.

[73] Assignee: The Charles Stark Draper Laboratory, Inc., Cambridge, Mass.

[21] Appl. No.: 836,220

[22] Filed: Sep. 23, 1977

[51] Int. Cl.² ............................................. G01N 19/02
[52] U.S. Cl. .................................. 364/551; 364/474; 364/111; 73/104
[58] Field of Search ..................... 364/474, 551, 111; 73/618, 104, 619

[56] References Cited

U.S. PATENT DOCUMENTS

| | | | |
|---|---|---|---|
| 3,430,035 | 2/1969 | Read | 364/111 X |
| 3,532,863 | 10/1970 | Enslein et al. | 364/551 X |
| 3,694,637 | 9/1972 | Edwin et al. | 364/551 X |
| 3,809,870 | 5/1974 | Auble et al. | 73/104 X |
| 3,841,149 | 10/1974 | Edwin et al. | 364/551 X |
| 3,866,829 | 2/1975 | Egawa et al. | 364/551 X |
| 3,986,010 | 10/1976 | Lankford et al. | 364/107 |

*Primary Examiner*—Edward J. Wise
*Attorney, Agent, or Firm*—Robert F. O'Connell

[57] ABSTRACT

A system for determining cutting-tool wear which utilizes a sensor for producing an output signal representing the cutting profile of the tool and a data processing system using microprocessor control which is responsive to the sensor for storing information concerning such cutting profile when the tool is initially installed and for comparing updated cutting profile information with the stored initial cutting profile information to provide output information concerning the wear characteristics of the tool. The wear information can be displayed, either visually or audibly, or can be supplied to an external data processor, such as the overall machine tool processor, for use therein. The system includes means for correcting errors which arise because of sensor and tool bit characteristics.

15 Claims, 30 Drawing Figures

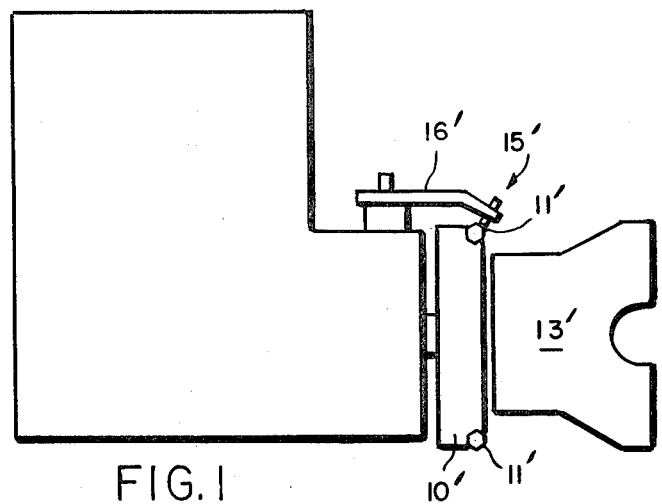
FIG. 1
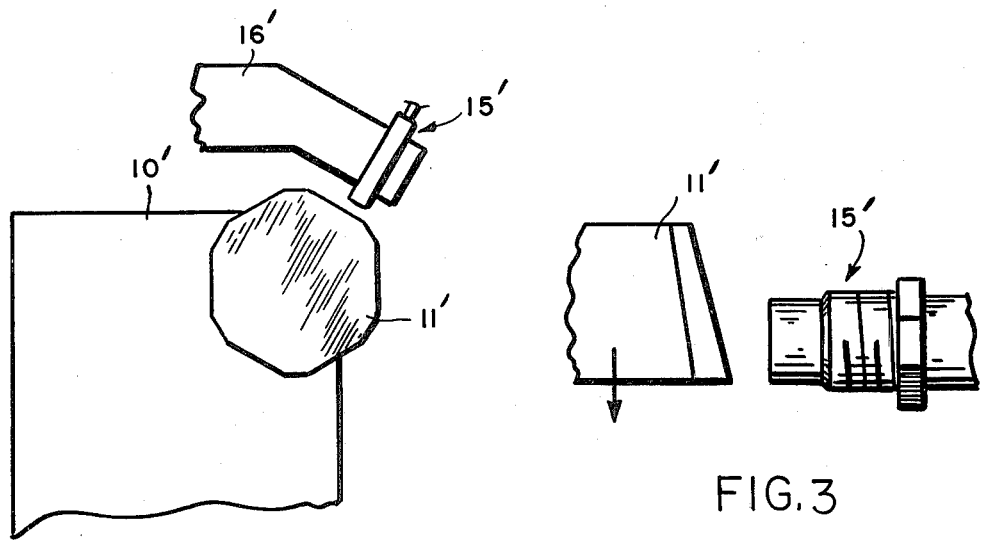
FIG. 2
FIG. 3
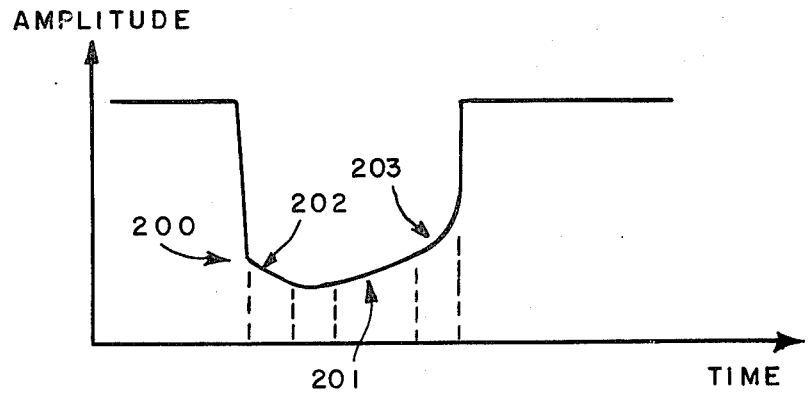
FIG. 3A

EXAMPLE FOR FOUR SAMPLES PER TOOL BIT

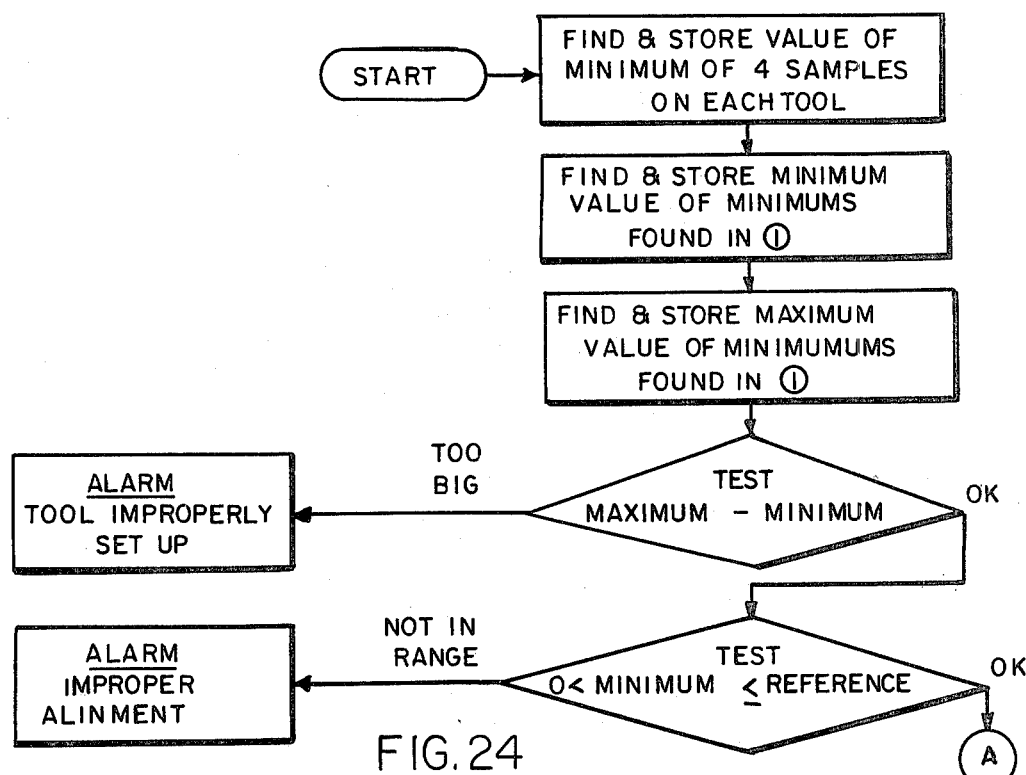
FIG. 24
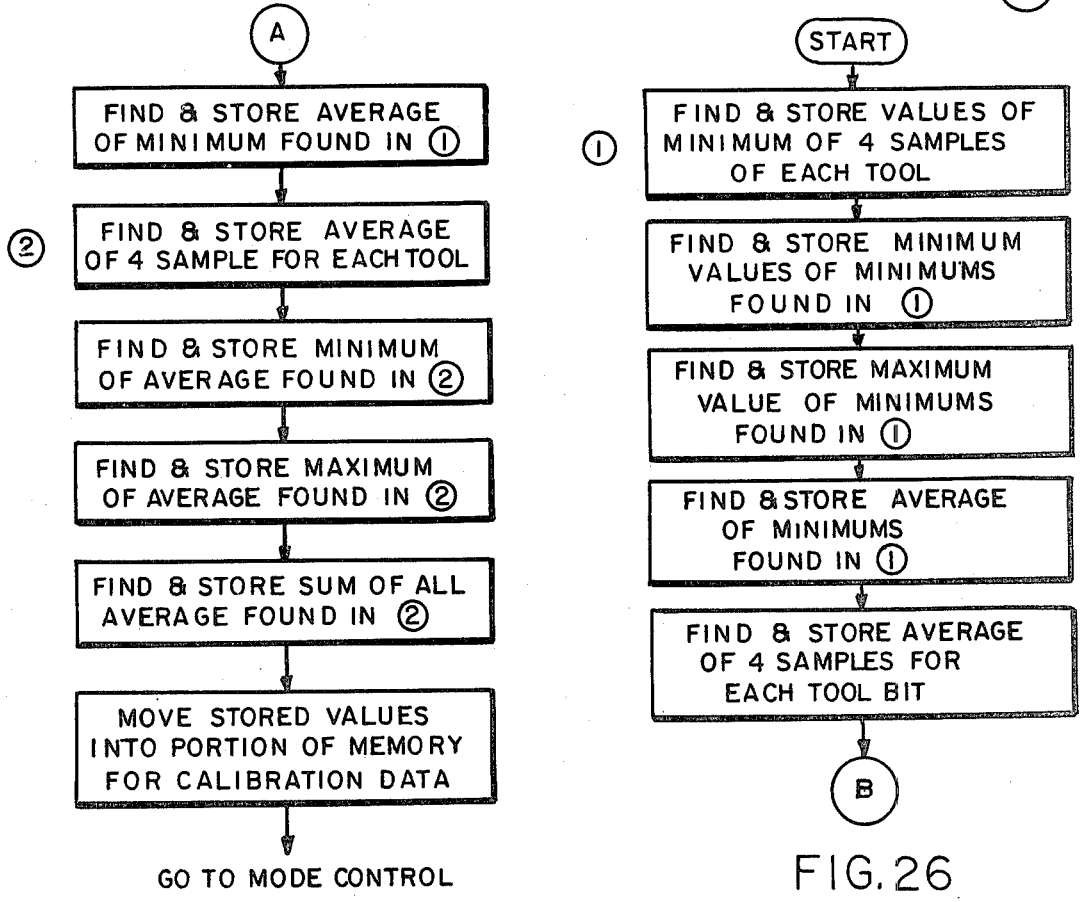
FIG. 25
FIG. 26

APPARATUS FOR DIRECTLY MEASURING MACHINE TOOL WEAR

INTRODUCTION

This invention relates generally to tool wear measurement techniques and, more particularly, to an apparatus for providing on-line tool wear measurements utilizing digital, microprocessing techniques.

BACKGROUND OF THE INVENTION

The increased use of automation in the metal-cutting industry has created a demand for effective means for providing on-line tool wear measurements. Suitable designed systems for continuously monitoring tool conditions during the actual operation of a machine should permit the use thereof by unskilled operators and the interfacing thereof with automatic machine tool control systems so that the machine can, in effect, monitor itself. Further, the wear on a tool plays an important role in determining how much time a machine must be shut down for tool changes. Moreover, premature wear or failure of a tool may cause several pieces which are being machined to be processed incorrectly, resulting either in their complete loss or a degraded quality. Accordingly, an effective on-line measurement of tool wear can permit better control of both operating costs and product quality in automated processes.

It is desirable to provide a tool wear monitoring system which is capable of providing an accurate and precise reading of tool wear during actual machine operation with a minimum of time delay in the tool wear detection process. Such a tool wear measurement device should provide high reliability at reasonable cost both in terms of its manufacturing and installation costs, as well as in its operating costs. The procedure for calibrating such a device should be relatively simple and automatic and consume minimal time of an operator who probably need not have maximum skills in the tool operating art.

Further, such a system should carry out its function without requiring changes in tool design that might adversely affect the cost of production. Such a device should provide minimum interference with the operating process for which the machine tool has been installed. Finally, such a system should be applicable in monitoring many different tools without modification either to the system itself or to the tools which are being monitored.

DESCRIPTION OF THE PRIOR ART

As discussed in co-pending application, Ser. No. 781,145 of D. Hamilton, et al, filed Mar. 25, 1977 and entitled "Production Tool Wear Detector" and assigned to the same assignee as this application, a summary of state-of-the-art techniques for sensing tool wear can be found in the publication "Survey of the State of the Art of Tool Wear Sensing Techniques", by N. Cook, et al., available from the Materials Processing Laboratory, Department of Mechanical Engineering, Massachusetts Institute of Technology, Cambridge, Massachusetts, September 1975, and prepared under National Science Foundation Grant No. GI-43861.

As discussed in the Hamilton, et al. application, the Cook, et al. survey reaches the conclusion that no satisfactory on-line techniques have been found which would provide reliable tool wear information, the techniques described therein primarily utilizing indirect cutting process parameters for determining tool wear rather than measuring dimensions of actual wear at the regions of the tool of interest. Any direct methods tend to measure the dimensions in various manners which have not permitted on-line operation or have provided difficult or impractical to implement in production line contexts.

In the Hamilton et al. application an approach to direct, on-line measurement techniques is described in which sensing means are utilized to monitor the distance from the sensing means to the cutting (i.e. wearing) surface of a tool and to monitor the distance from the sensing means to a nonwearing reference surface of the tool. Such distances are then processed in a manner which provides for an accurate determination during actual use of the wear characteristics of the tool which is being monitored.

While such a system provides relatively reasonable costs and conceptual simplicity, certain problems inherently arise therein which make it unsuitable in many applications. Thus, the system relies on the stability and accuracy of several timing and linear elements in its electronics which elements, besides having to operate in the thermal and noise environment of a shop floor, must also be adjustable to allow calibration and adaptation to different tool types if flexibility in use of the monitor is to be achieved.

Further, such system does not correct for sensor non-linearities which have been found in many cases to be a significant factor in affecting the accuracy of the tool wear measurement. Moreover, the system is not always easy for an operator to use and to calibrate and is subject to operator miscalibration as well as to sensor misalignment. In addition, while such system provides a good determination of leading edge tool wear, it is less satisfactory in determining fractional edge wear or flank region wear.

Since the previously disclosed Hamilton et al. technique utilizes large numbers of discrete components, its hardware complexity may be a disadvantageous factor for many applications. The system is also sensitive to gain and offset errors as well as to timing errors and requires a more complex calibration procedure, as well as other adjustments, when changing tools of the same type or when changing to a different tool type. Accordingly, its inability to provide flexibility of performance for many different tool types adds a further disadvantage in many applications. Further the Hamilton et al system preferably requires the use of two sensors or, if only one sensor is used, such system requires that the tool itself be modified to provide a mechanical reference surface.

BRIEF SUMMARY OF THE INVENTION

This invention overcomes many of the disadvantages of the tool wear measurement systems suggested by the prior art and represents an improvement in the general technique described in the Hamilton, et al. application, while retaining the advantages which result from using eddy current type sensors, as described in more detail below. The invention also provides the advantage of using a single sensor without requiring any modification of the tool itself. In accordance with the invention, a sensor output signal is converted to digital form, the digital data information being appropriately processed by an appropriate microprocessor utilizing suitable associated random-access-memory (RAM) and read-onlymemory (ROM) units. The microprocessor unit can provide tool wear measurement determinations for suitable visual display with respect to each tool bit of a machine tool. It also can provide for alarm activation when one or more of the tool bits, or the average wear of the tool bits, on a particular machine tool exceeds predetermined limits.

The microprocessor unit acquires the required data samples by an analog-to-digital conversion process and appropriately formats the data and stores it into the random-access-memory unit. The microprocessor then acquires the desired data processing programs, which are stored in the read-only-memory unit, such programs thereupon correcting the sensed data in accordance with the particular sensor and tool characteristics which are being utilized and comparing the data which has been so corrected with data taken during an initial calibration of the system. The results of such processing are then displayed numerically, as oscilloscope patterns, or as alarm signals for use by an operator or machine tool control computer, as desired. Moreover, the invention can be utilized to detect not only continued wear on tool bits, but also the fact that there are missing or broken tool bits.

Since a programmed microprocessor is utilized, changes in the calibration and processing programs can be readily made for use with different tools which are to be monitored. The programs can be run with accurate reference to time by utilizing a suitable digital crystal clock so that the sensor outputs can be sampled with accurately determined delays and sample apertures. The changing of such programs can be readily performed without changing the hardware which is being utilized.

The hardware units which are required are readily available at reasonable cost and the processing requirements may in some cases be at least partially implemented within the machine tool's own control computer, if the machine tool installation already has one.

The system of the invention utilizing the microprocessor approach permits appropriate correction of the data so that processing of flank wear information as well as leading edge information can be performed. Calibration problems are greatly reduced by utilizing the system's ability to "memorize" the profile characteristics of a newly installed tool, which characteristics can be stored for use in the subsequent tool wear determination process which occurs during actual cutting operation so that no requirement for shutting down the machine tool is necessary. Furthermore, only one sensor need be used with no mechanical reference, the "memorized" characteristics being used as the reference information.

The system can be utilized by a human operator who is not required to have maximum skill in the tool operating art. The system is simple and easy to use, either by a human operator or by a process computer which may already be in use in the machine tool installation. Also the system can in effect check itself so as to insure proper operation by an operator.

In view of the large amount of information that can be obtained from using the system of the invention, the overall manufacturing, installation and operating costs can be held to reasonable levels which make the system reasonably comparable and competitive with any tool wear measurement system presently suggested for use by the prior art.

The invention can be described in more detail with the help of the accompanying drawings wherein:

FIGS. 1 and 2 depict in a diagrammatic manner a typical machine in which the invention can be used;

FIG. 3 depicts in more detail a portion of the machine shown in FIGS. 1 and 2;

FIG. 3A depicts a typical tool bit profile;

FIGS. 20-22 and 24-28 depict flow charts of various typical programs used in the system of the invention.

Figure 4:
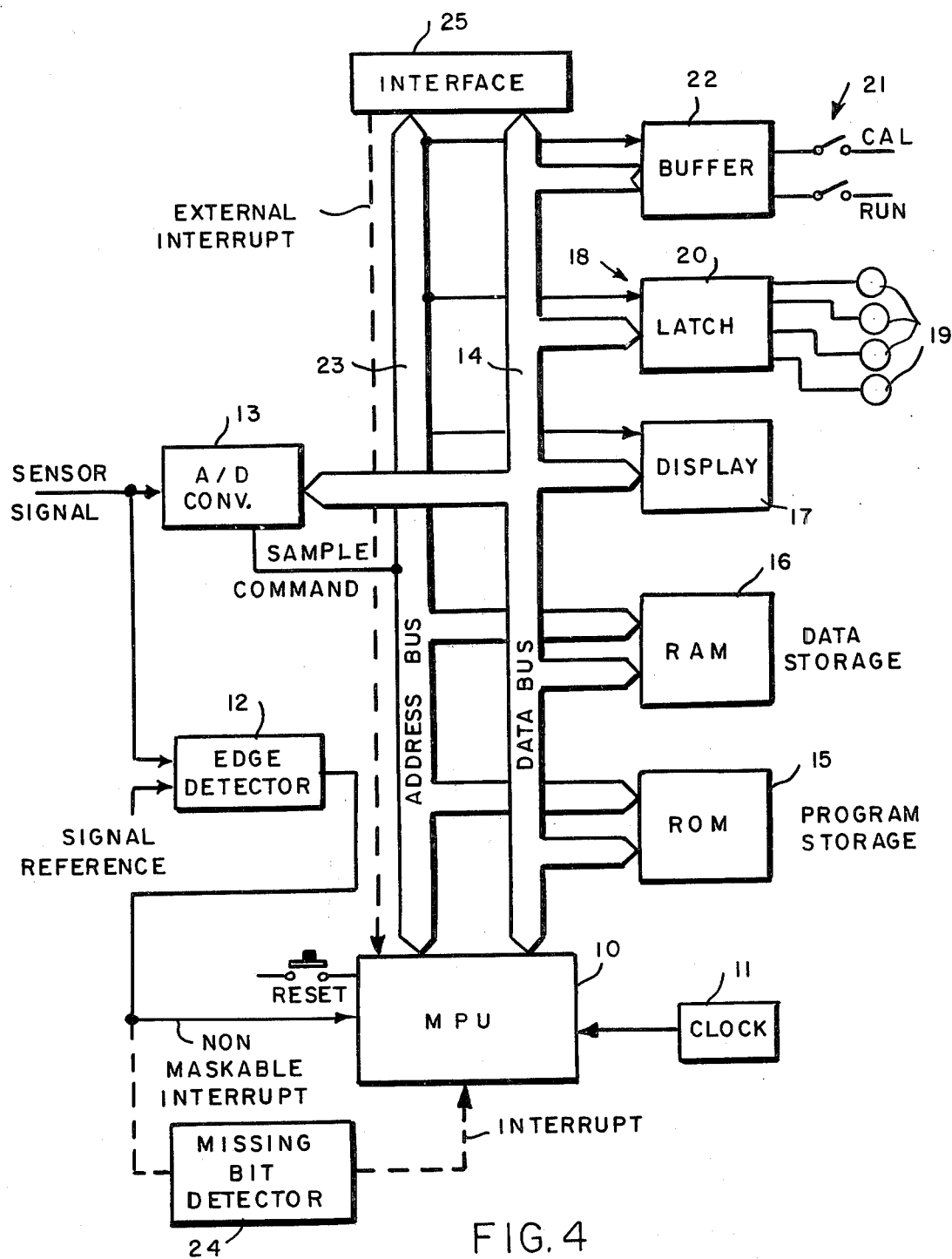
FIGS. 4 and 6 depict in a block diagram form a particular embodiment of the overall system of the invention.

In FIG. 1, a tool wear measurement system in accordance with the invention is shown in diagrammatic form in an environment for determining the wear characteristics of tool bits on a milling machine tool. Thus, the milling machine comprises a rotary tool member 10' having a plurality of cutting tool bits 11', each with an appropriate cutting surface mounted so as to provide cutting action against a suitably mounted work piece 13'. The rotary member rotates in a plane perpendicular to the paper, the specific structure of such machines being well known to those in the art so that it need not be shown or described in more detail here. A sensing means 15' is appropriately mounted on a suitable arm 16' affixed to the machine, as shown and discussed in more detail with reference to FIG. 2.

The latter figure shows a portion of the rotary member 10', as well as one of the tool bits 11'. The sensing arm 16' holds the sensor means 15' which is mounted adjacent the tool bit 11' as it passes thereby during the rotary motion of member 10'.

In a typical milling machine the rotating face mill tool member 10' may consist of 34 tool bits arranged at equal distances around the circumference thereof. A typical tool bit 11', as shown in FIG. 2, comprises a hexagonally shaped C2 carbide bit which has six cutting edges. The tool bit orientation on member 10' can be changed when an edge is worn and the tool bit reclamped on member 10' so as to present a new edge to the workpiece, the tool bit being discarded when all of the edges are worn out.

The tool bit profile, as seen by the sensor, is shown in FIG. 3. A typical individual bit profile wave form obtained from the sensor means 11' is shown in FIG. 3A for a tool exhibiting some wear characteristics. As can be seen therein, the leading edge region is identified by reference number 200 and the flank region identified by reference numeral 201. Both leading and trailing edges have a transition region identified as 202 and 203, respectively. A plurality of such wave form profiles for each of the bits on the machine tool will be received from the sensor for each revolution of the machine tool head.

A system in accordance with the invention for processing the sensor wave form information of the type shown in FIG. 3A is shown in FIG. 4. As seen therein, the system of the invention includes a microprocessor unit (MPU) 10, the operating time cycle thereof being controlled by a clock signal from a suitable clock 11 which may be a crystal clock circuit, for example. The sensor output signal has its leading edge detected by a suitable detector circuit 12 for providing an interrupt signal to the MPU 10. The sensor output is converted from its analog waveform to a digital signal by a suitable analog to digital (A/D) converter 13. Converter 13 is connected to a system data bus 14, the latter also being connected to the MPU 10, to a read-only-memory (ROM) unit 15, to a random access memory (RAM) unit 16 and to various peripheral output units, such as a data display unit 17, an alarm unit 18 having appropriate alarms 19 and latching circuitry 20, and a control switching unit 21 via buffer unit 22 for placing the system into a calibration (CAL) or a RUN mode of operation. A system address bus 23 is also connected to the same units. A missing tool bit detector unit 24 may also be connected from the sensor to the microprocessor unit 10, although in certain embodiments this detector unit may be omitted. The system may be interfaced with the machine tool controls via the address and data buses, in certain applications using an external interrupt line as shown by the dashed line, through an appropriate interface unit 25.

In the system of FIG. 4, the edge of the sensor output waveform is used to initiate action in the data sampling process. In this case, the action is in the form of an interrupt signal sent to the microprocessor (MPU) unit 10 which causes the latter unit to acquire a selected program which is stored in read-only-memory unit 15. The selected program services A/D converter 13 by calling the converter on the system address bus 23 and providing a command to sample the data in the sensor waveform. When converter 13 has acquired the data sample (or samples), the A/D converter 13 places the data onto data bus 14 for supply to MPU 10 which then formats the data and stores it in random access memory unit 16. The MPU then acquires the desired data processing programs which are also stored in ROM unit 15.

The data processing programs are devised to correct the sensor data in accordance with the particular sensor and tool characteristics by using a suitable transfer function "lookup" table or by a suitably devised algorithm. Averaging of the corrected data can be done over periods determined by tool bit counting or MPU clock time. Once the data has been so processed, testing can be done to compare the results with data taken during the initial calibration of the system. The results of the tests, as well as the processed data, can be displayed as alarm signals or as data numbers for use by an operator or machine tool computer.

Since the system is programmed, any changing of the algorithm can be easily done. Thus, many different algorithms can be stored and selectively called by the mode command switch unit 21. In normal operation, the mode command switch 38 (FIG. 6) controls the MPU operation so that the data is used for calibration purposes or for tool wear processing, the switch also controlling what algorithms are to be used in processing the data.

Since the MPU is crystal clock controlled, the programs are run with an accurate reference to time. This allows the A/D converter service programs to sample the sensor output with accurate delays and sample apertures. Again, because this is performed by suitable programs, the programs can be altered by changing the programs without changing the hardware.

The detection of a broken or missing bit in the tool can be done with a missing tool bit detector unit 24 or with a suitable timing program in the MPU 10 and ROM unit 15, the choice of method depending on the program architecture.

Hardware requirements for such a system are easily met by a large number of commercially available microprocessors. An eight-bit machine with 512 words of ROM and 256 words of RAM is adequate to allow for self-calibration, data correction, and processing by peak value detection and averaging. A low cost eight-bit successive approximating A/D is also adequate. The requirements and selection of suitable devices are discussed below.

Because of the modest processing requirements, the approach shown in FIG. 4 also can be partially implemented within the machine tool's own control computer if it has one. Thus, the invention, besides being compatible with the machine tool control interface, may also be compatible with the machine tool controller function itself. By proper choice of frequency, the crystal clock 11 can be shared with the sensor, further reducing the cost and complexity.

Figure 5:
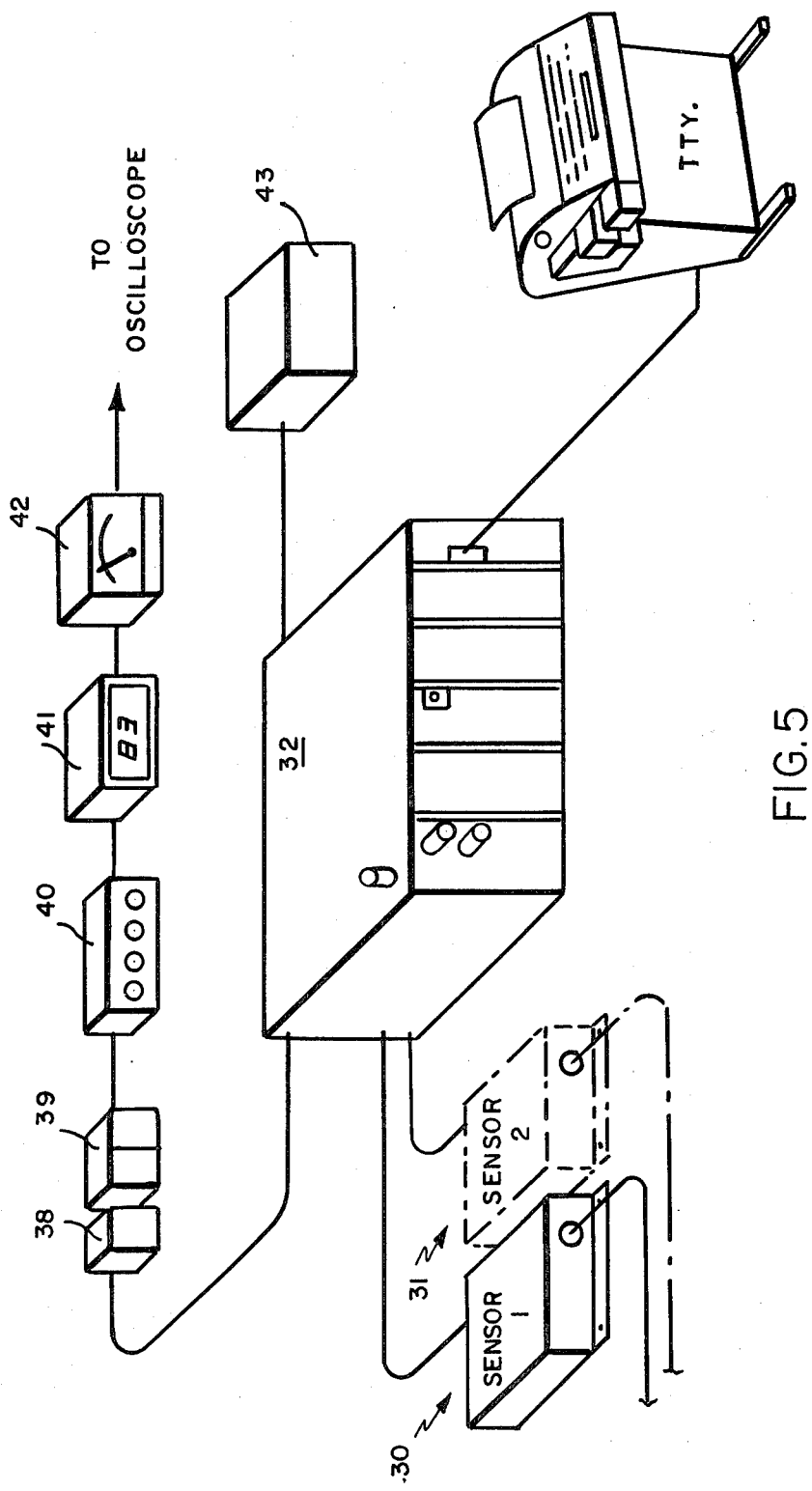
FIG. 5 depicts in diagrammatic perspective a particular embodiment of the overall system of the invention.
Figure 6:
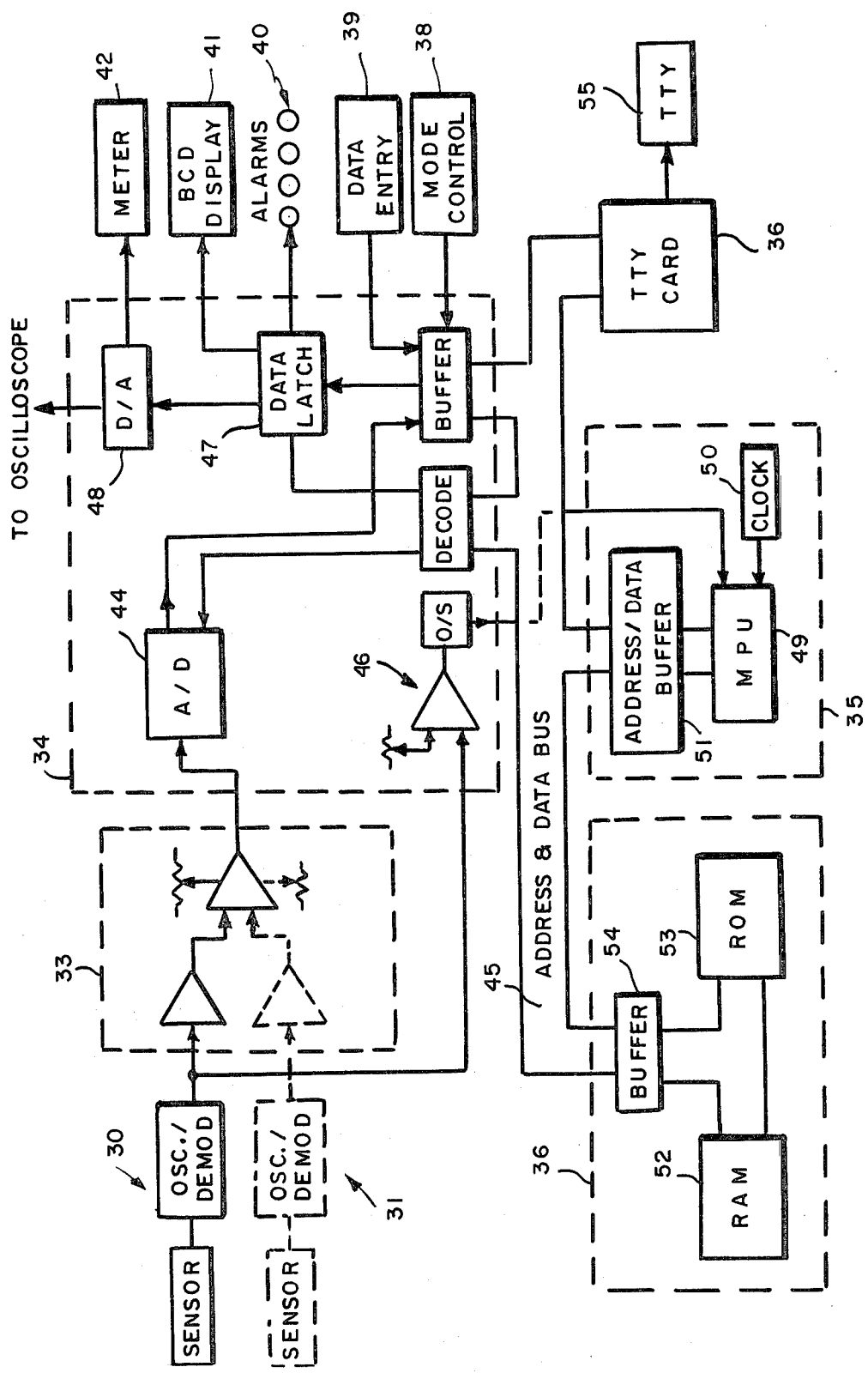

The arrangement of the basic elements in a typical system in accordance with the invention is depicted in simple pictorial form in FIG. 5 and in block diagram form in FIG. 6.

A single machine tool profile sensor module 30, including appropriate demodulation circuitry, utilizes an eddy current probe such as manufactured and sold, for example, under Model designation KD-2300-.5SU, by Kaman Sciences Corporation of Colorado Springs, Colorado. Although a pair of sensors may be used, because of cost and complexity, a single sensor system is preferable. In FIG. 5, the second sensor 31 is shown in phantom and is of the same type as the single sensor 30. The outputs thereof are supplied to amplifier card 33 (FIG. 6) which can provide suitable differencing of the two outputs and suitable switching to allow for the use of either or both sensor outputs. The circuitry for dual sensor operation is shown in phantom in FIGS. 6 and 7.

The output of the sensor module 30 is connected to the processing electronics unit 32, which consists of five card modules, discussed below, held in a rack mountable assembly. An amplifier card module 33 provides suitable amplification of the output signal from the sensor.

An A/D and I/O card module 34 provides the input and output (I/O) interfaces for the microprocessor unit. The amplified sensor output signal (or difference signal if two sensors are used) from amplifier card module 33 is connected to an eight-bit successive approximating analog-to-digital converter 44, the output of which is connected to the system address and data bus 45. The sensor signal is also connected to a variable threshold edge detecting circuit 46 on card 34 to provide the microprocessor with the information that the tool bit profile is present and requires processing. The circuitry necessary to operate the input mode control and data entry switches 38 and 39 is also included on card 34 for connecting such switches to the system data and address buses to provide command and data entry to the microprocessor. Latch circuitry 47 on card 34 hold output data from the microprocessor and drive an alarm display unit 40 and a two-digit binary coded decimal (BCD) display unit 41. An analog output from the microprocessor is supplied by a latch circuitry 47 and eight-bit digital-to-analog (D/A) converter 48 on card 34 for connection to a meter unit 42 and/or to an oscilloscope (not shown) displaying the data in analog form.

A microprocessor unit card module 35 contains the microprocessor circuit 49 as well as its clock circuitry 50. The data and address outputs of the MPU are suitably buffered by buffer 51 to allow adding other external card modules to the system buses and to prevent damaging of the MPU should the buses be inadvertently shorted during use or experimentation with the system. The MPU card module 35 also has a reset switch 43 (FIG. 10) that overrides all program activity and can prove useful when an operator is developing programs which may not work properly when first tried.

A memory card module 36 contains in a typical embodiment 3072 words of memory. Such storage capacity is provided, for example, as 1024 words of random-access-memory (RAM) 52 and 2048 words of read-only-memory (ROM) 53. The ROM memory which is used can be of the erasable and reprogrammable type. In normal program development, after a program has been fully developed using the RAM, the program is loaded into the ROM using a suitable programming device designed for the type of ROM used. The ROM allows permanent storage of the program as opposed to the RAM, which loses its stored contents whenever the power to the system is turned off. Should changes be necessary to the program stored in ROM, the ROM can be appropriately erased, after which the new program is entered. Such a ROM unit is commonly referred to as a PROM (i.e., a programmable read-only-memory).

As in the MPU card, the data inputs and outputs of the memory card module are fully buffered by buffer 54 to allow the use of additional memory card modules and to prevent accidental damage to the memory. Provision can also be made in the MPU card module to move the address location of the memories should additional memory be used.

A Teletype card module 36 contains the circuitry necessary to interface with a standard commercially available teletype unit 55 having a conventional keyboard, typewriter and paper tape punch/reader. The card module 36 may also contain RAM and ROM units (not shown) that can be used to provide support programs that operate the teletype. These programs allow changing the system memory contents and reading of registers within the MPU. These programs are used for the development of the programs that will be used in the system for a specific application. Once the program is developed and stored in the PROM, the TTY card module is no longer required and the system can operate using its own I/O entry and display devices.

A power supply 43 (FIG. 5) is a three output commercially available power supply to operate all of the electronics in the system, including the sensors. The supply voltages required in a typical system, for example, are +5, +15 and −15 volts DC. All other voltages required by the system can be generated with internal regulators.

The system of FIGS. 5 and 6 is designed to be bus oriented so as to allow the addition of more electronic functions without requiring major changes to the system. The interconnections among all digital cards are performed by the bus system which comprises all the data and address lines. Timing lines needed by one card can also be brought to all the others for later use if modifications are required. While such an arrangement results in more interconnections than appear necessary for the original system design, the impact of changes during later development is reduced.

Figure 7:
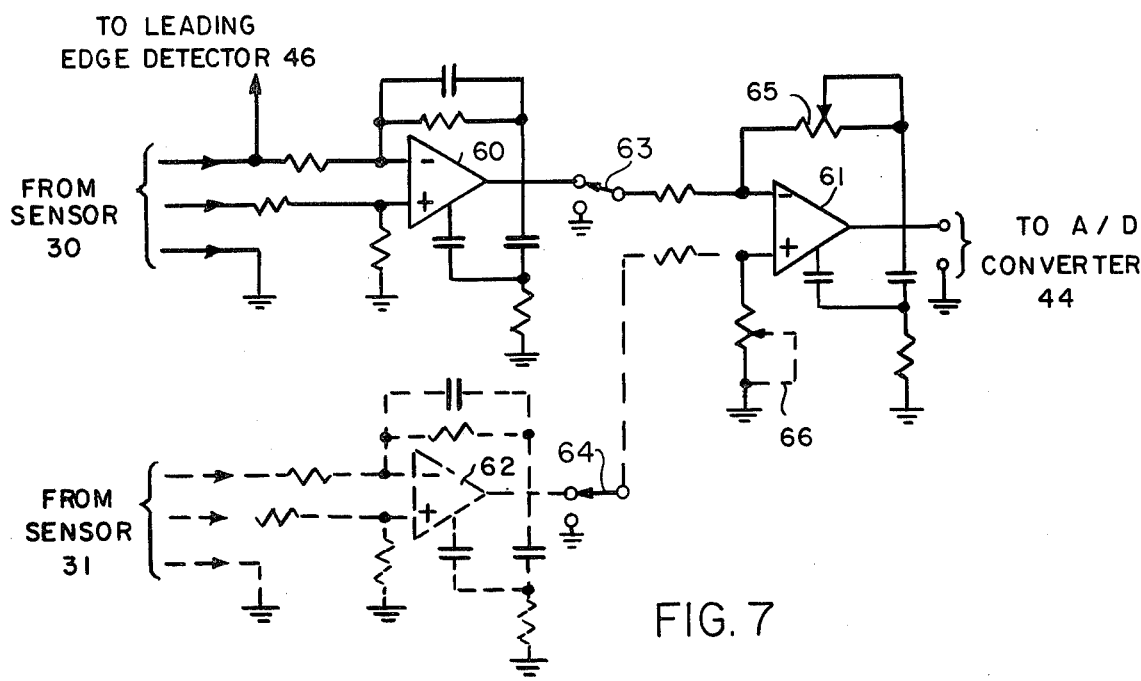
FIGS. 7-12 depict logic diagrams of various portions of the particular embodiment of the system shown in FIGS. 4 and 6.

The amplifier card 33 is shown in schematic form in FIG. 7. Amplifiers 60 and 61 amplify the signal from twisted-shielded pair lines from sensor 30 for a single sensor operation to provide an output signal having a suitable gain. If two sensors are used the output from second sensor 31 is supplied to amplifier 62 and the outputs from amplifiers 60 and 62 are supplied through a pair of switches 63 and 64, respectively, to an amplifier 61 which in such case would be a differential amplifier. The switches allow selecting either sensor signal or both as inputs to amplifier 61 which takes the difference between the two signals (or the values thereof relative to ground) and inverts and amplifies by a suitable gain set by variable resistors 65 and 66, (e.g. precision multi-turn potentiometers). The output from amplifier 61 is used as the input to A/D converter 44 on card module 34. The gain of the overall amplifier card as shown is non-inverting if only the upper single sensor channel is selected and is inverting if the lower second sensor channel is also used. Frequency and stability compensation for the amplification circuitry is provided by the resistor-capacitor networks shown.

Figure 8:
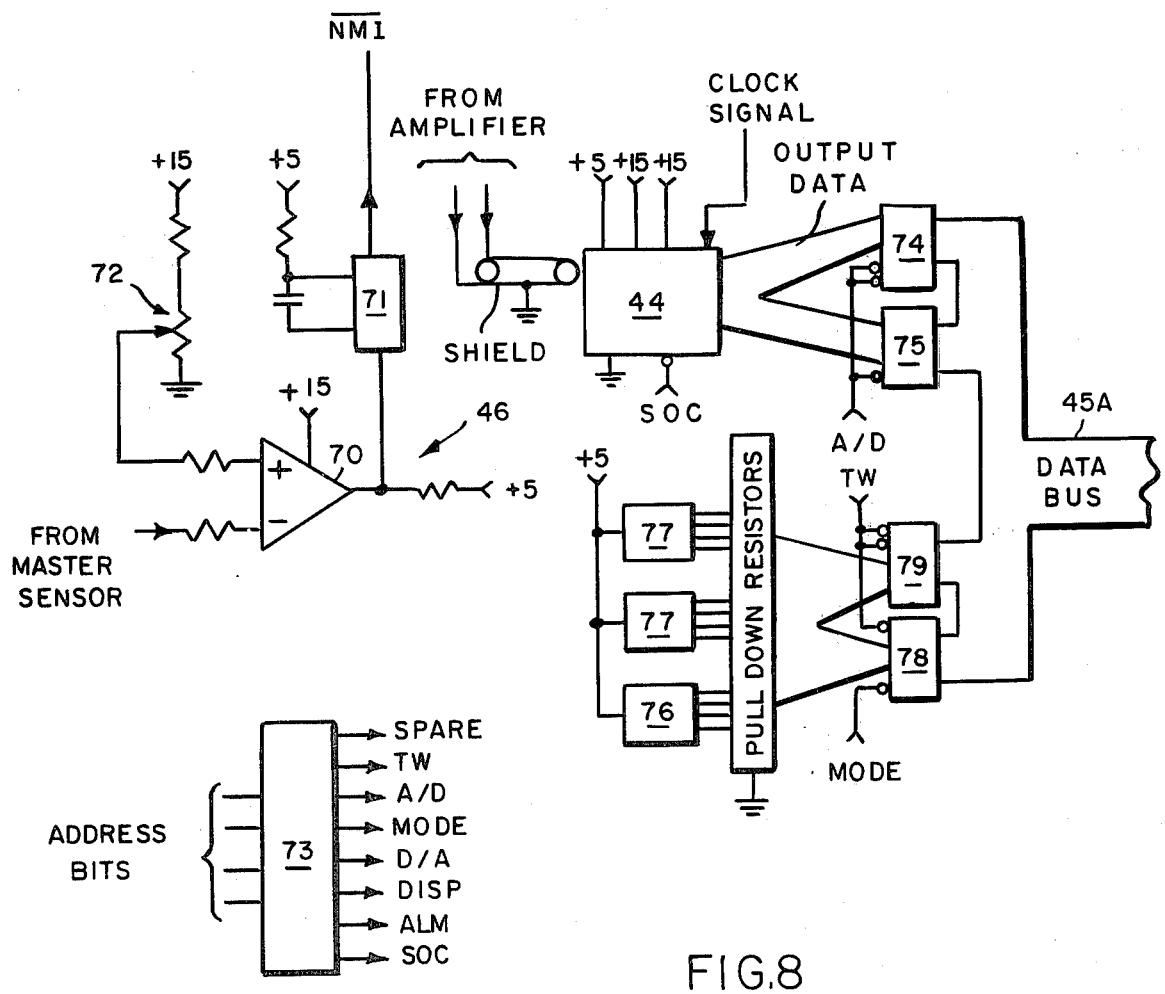
Figure 9:
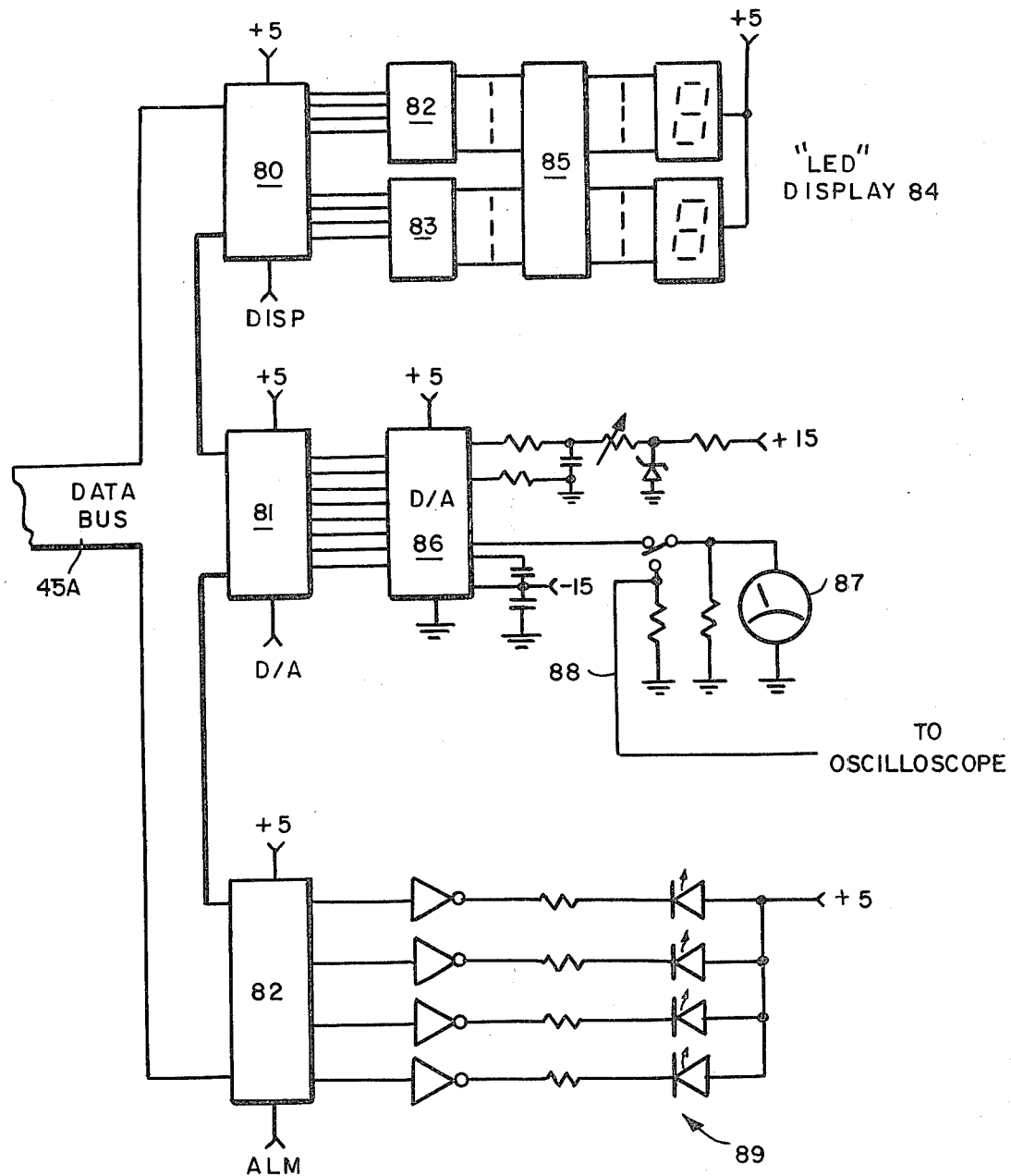

The A/D and I/O card module 34 is divided into two sections, i.e., an input section shown in FIG. 8 and an output section shown in FIG. 9. In the input section comparator 70 and multivibrator 71 comprise leading edge threshold detector 46 and provide a microprocessor interrupt signal when a tool bit profile signal from sensor 30 occurs at the input to comparator 70. The voltage at the comparator input is compared with the voltage level set by potentiometer 72. When the input threshold is exceeded, the output of comparator 70 changes state and triggers multivibrator 71, a one-shot multivibrator which produces a negative going pulse when its input goes from the low to the high state. The pulse created by the one-shot 71 produces a microprocessor non-maskable interrupt ($\overline{\text{NMI}}$) signal. When the MPU receives the non-maskable interrupt signal, it stops whatever program it is working on, stores the information necessary to continue the program later and jumps to a program that services the A/D converter on card 34. When the data is taken from the A/D converter and stored in memory, the microprocessor returns to whatever program it was performing before the interrupt and continues. An $\overline{\text{NMI}}$ command always has highest priority during processing operations and cannot be overridden by any program because data obtained by the A/D converter on the input tool bit waveform always is given highest processing priority.

The output signal from amplifier card 33 is connected to the input of the A/D converter 44. When a request for A/D data is sent by the microprocessor over the address bus, the address decoder unit 73 commands the A/D converter 44 to begin its operation. After a time delay, determined by the A/D converter operating speed, the data therefrom becomes available at the output lines which are buffered and supplied to the system data bus 45A by buffers 74 and 75. The microprocessor then calls the buffer address via the address decoder 73 and the data is placed onto the data bus 45A to be read by the microprocessor.

The A/D converter 44 operation is clocked by the crystal clock 50 on the MPU card 35. The voltage at the input thereto is converted, for example, to an eight-bit digital number in eight clock cycles after receipt of its command to start. Thus, for a 1 MHZ, clock, conversion of the input would take 8 microseconds from the command to start.

Mode control and data entry switches are shown as switch circuits 76 and 77, respectively. For example, the mode control switch 76 can be a ten-position BCD thumbwheel switch which allows the selection of several different processing and diagnostic modes of operation. Switch 77 can consist of two ten-position BCD thumbwheel switches which allow entry of numbers from 0 to 99 into the microprocessor programs. The mode control and data entry switches are buffered and supplied to the data bus 45A by buffers 78 and 79. The microprocessor calls for the data on these switches via the address decoder 73.

The output section of the A/D and I/O card module 34 is shown in FIG. 9. When the microprocessor is required to display a data word as an output, the address decoder 73 of FIG. 8 activates one of the latch circuits 80, 81 or 82 which stores the data word therein. The data word stored in latch 80, for example, operates a two-digit BCD numerical display after decoding by decoder circuits 82 and 83 and supply to light emitting diode (LED) display unit 84 via current limiting circuitry 85. Analog output is provided by latch 81 which is connected to an eight-bit D/A converter 86 which drives a meter 87 and also provides a sampling point 88 for the connection of an oscilloscope. The data stored in latch 82 provides alarm information that controls the alarm light circuitry 89.

Figure 10:
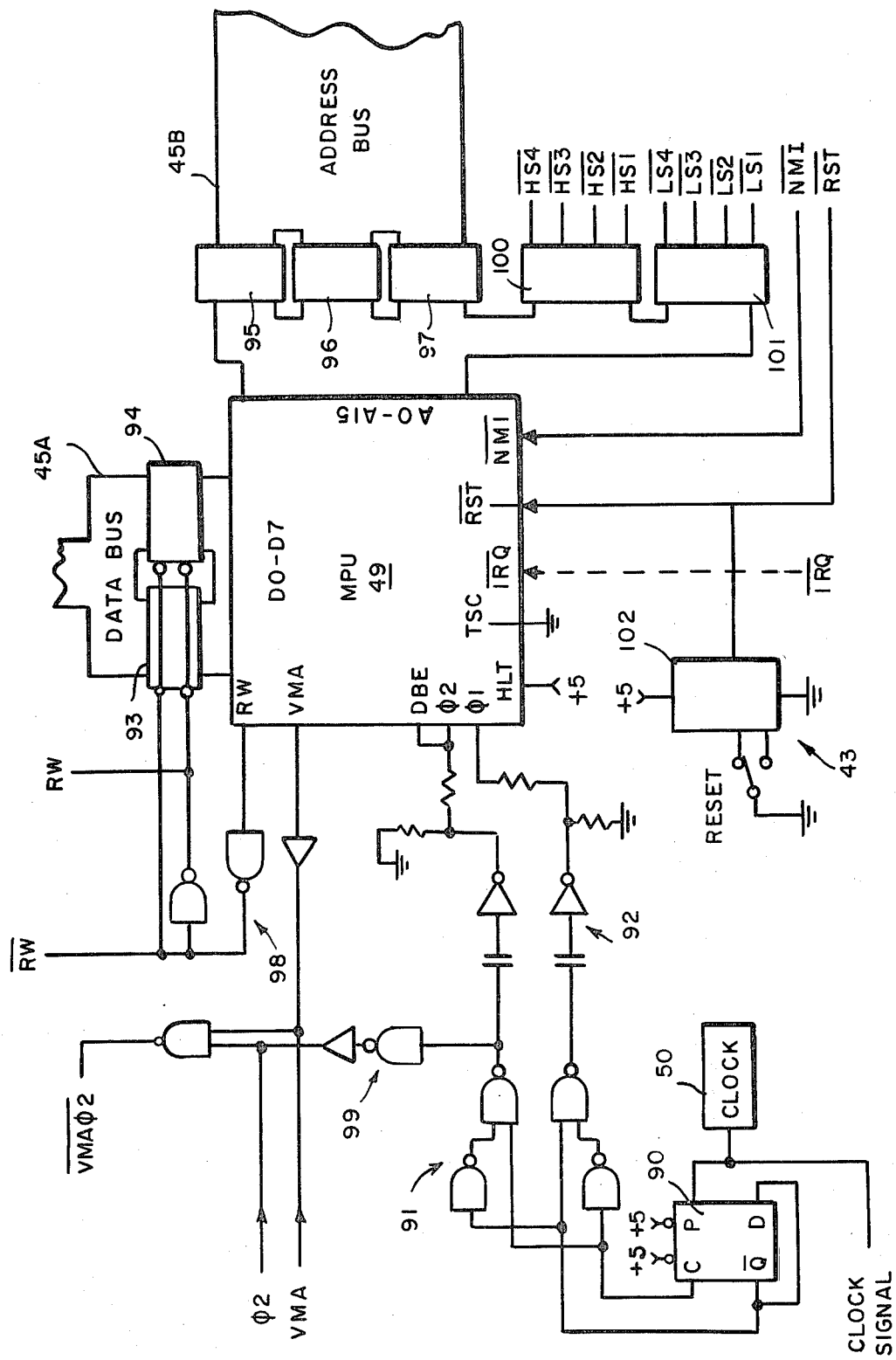

The microprocessor and its support electronics are shown on MPU card 35 as depicted in FIG. 10. The microprocessor unit 49 can be, for example, a unit manufactured and sold under the model designation M6800 by Motorola Semiconductor Products, Inc., Phoenix, Arizona. Such a microprocessor has an eight-bit data bus 45A and a 16-bit address bus 45B. It is capable of operating with memories of up to 65,536-bit words capacity. The capabilities and architecture of the M6800 are briefly described later in connection with the algorithms used with the processing system. Other processors are available which are compatible substitutes for the M6800. The machine cycle time for the M6800 is one clock period of its two-phase clock, i.e., 2 microseconds. The clock is derived from the 1 MHZ. crystal oscillator, through a frequency divider 90, and a non-overlapping phase splitter 91. The TTL logic levels are converted to MOS levels by amplifier circuitry 92. The actual clock frequency used is 0.5 MHZ at the input to the M6800, for example. The frequency used is about one half the maximum for the M6800 to allow the use of slower, less expensive memories.

The data and address lines of the microprocessor are buffered by buffers 93–97 to permit the supplying of the bus to external cards and to protect the processor from the accidental shorts. The read/write lines ($\overline{RW}$ and $RW$) and several timing lines (VMA, $\phi 2$, $\overline{VMA\phi 2}$) are buffered by buffers 98 and 99. Partial address decoding of the more significant bit address lines is done by decoder circuits 100 and 101, the use of which permits the use of less decoding circuitry on the other cards in the system.

The system reset switch 43 is debounced by debouncer 102 and connected to the microprocessor. The $\overline{NMI}$ line is brought out directly onto the system bus. A lower priority maskable interrupt signal $\overline{IRQ}$ is not always used but is available for use if a lower priority interrupt is required, or it can be connected to a missing tool bit detector or interfaced with an external computer.

Figure 11:
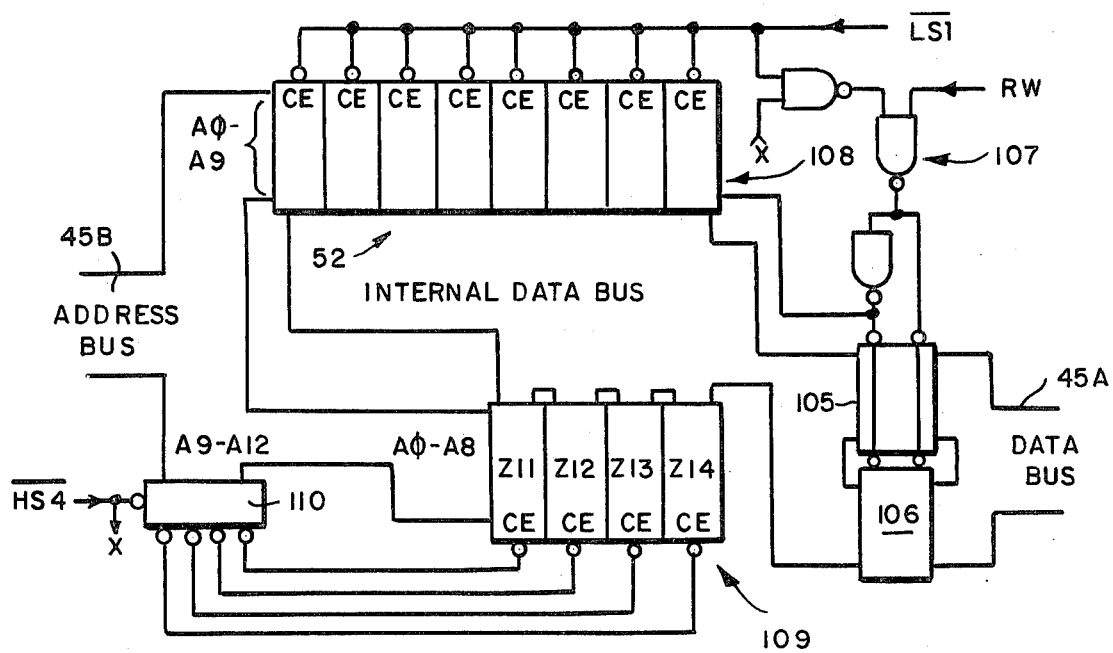

The circuitry on the memory card 36 is shown in FIG. 11. Connection to the system data bus 45A is through bi-directional buffers 105 and 106. The bus read/write line (RW) selects the correct data mode via logic circuitry 107.

The RAM 52 of the memory card 36 comprises eight integrated circuits 108 which contain 1024 8-bit words of storage. Selection of this portion of memory is done with the address lines $A\phi$–A9 and an enable line $\overline{LS1}$ derived from the lower address bits in the MPU card 35.

Programmable ROM (PROM) 53 comprises four integrated circuits 109 containing 2048 8-bit words of ultraviolet light erasable memory. Selection of this memory is done with address lines $A\phi$–A8 and A9–A12 which latter bits are decoded by decoder 110 for enabling the PROM. The enabling of the ROM is controlled by the $\overline{HS4}$ line derived from the upper three bits of the address which are decoded in the MPU.

Access time to read or write data into the memory for the system described in 2 microseconds. The devices used can actually operate faster than this but not fast enough to operate at the full speed of the microprocessor. The system clock has been slowed down to use these slower but less expensive memories in this particular embodiment since the process requirements normally do not require the full speed capabilities of the microprocessor in most applications in which the system is to be used.

Figure 12:
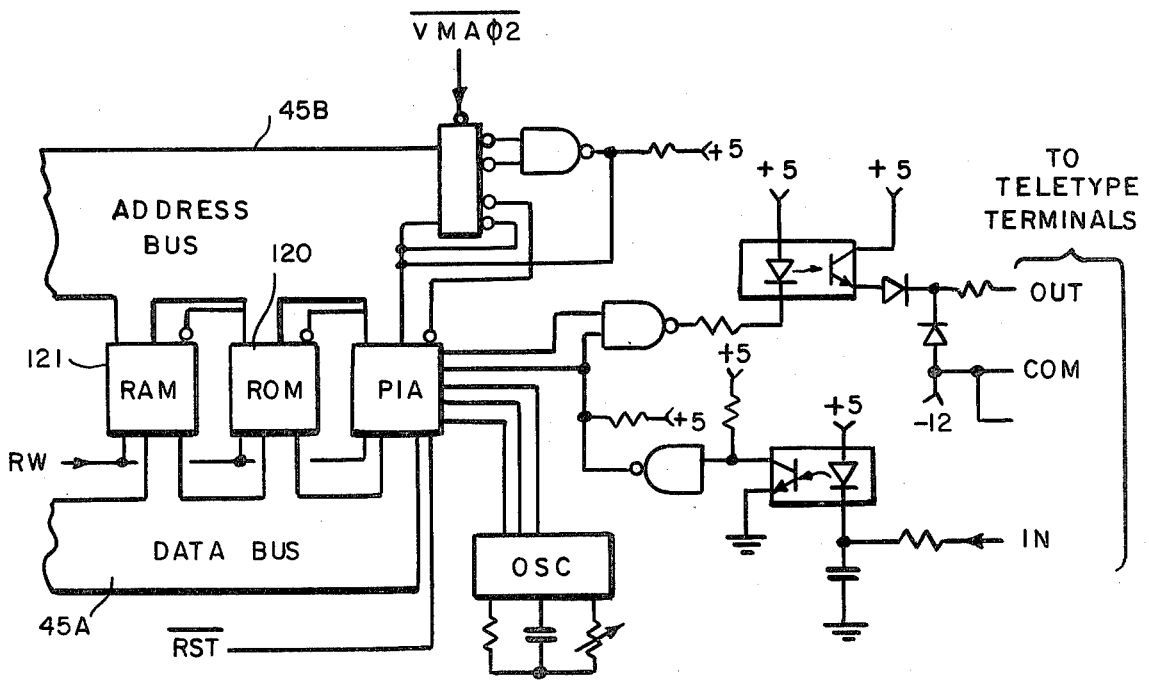

An interface suitable for conventional 20 ma. current loop asynchronous serial teletype terminals is shown as teletype card 37 in FIG. 12. For normal program development, a keyboard, typewriter, tape punch and tape reader are used. The interface circuits used are a variant of the design provided by Motorola Semiconductor Products, Inc. (identified by Motorola Model descriptions MCM6830L7 and MCMG810, respectively). A Motorola designed support program, MIKBUG, allowing user interface with the Motorola microprocessor identified above, is provided in a ROM unit 12 and small RAM unit 121 on the card. The MIKBUG program contains:

1. A memory loader, allowing entry into memory from paper tapes.

2. A register dump, which allows printing of the microprocessor registers associated with a target program.

3. A print/punch dump, used to print or punch a tape with the contents of user-addressed blocks of memory.

4. A program control, allowing the running of programs loaded into memory by the user.

5. A vector loader, which allows the user to specify address pointers for restart, non-maskable interrupt and interrupt request programs.

6. A memory change function, allowing the user to look at or change the contents of individual locations of memory for editing and debugging.

After a program has been developed and debugged using the Teletype card module 37, the program is dumped on tape and entered into the programmable ROM section of memory using a ROM programming machine. The Teletype card is then removed and the ROM is inserted into the memory card. The program can then be run using full microprocessor control for the given application.

Figure 13:
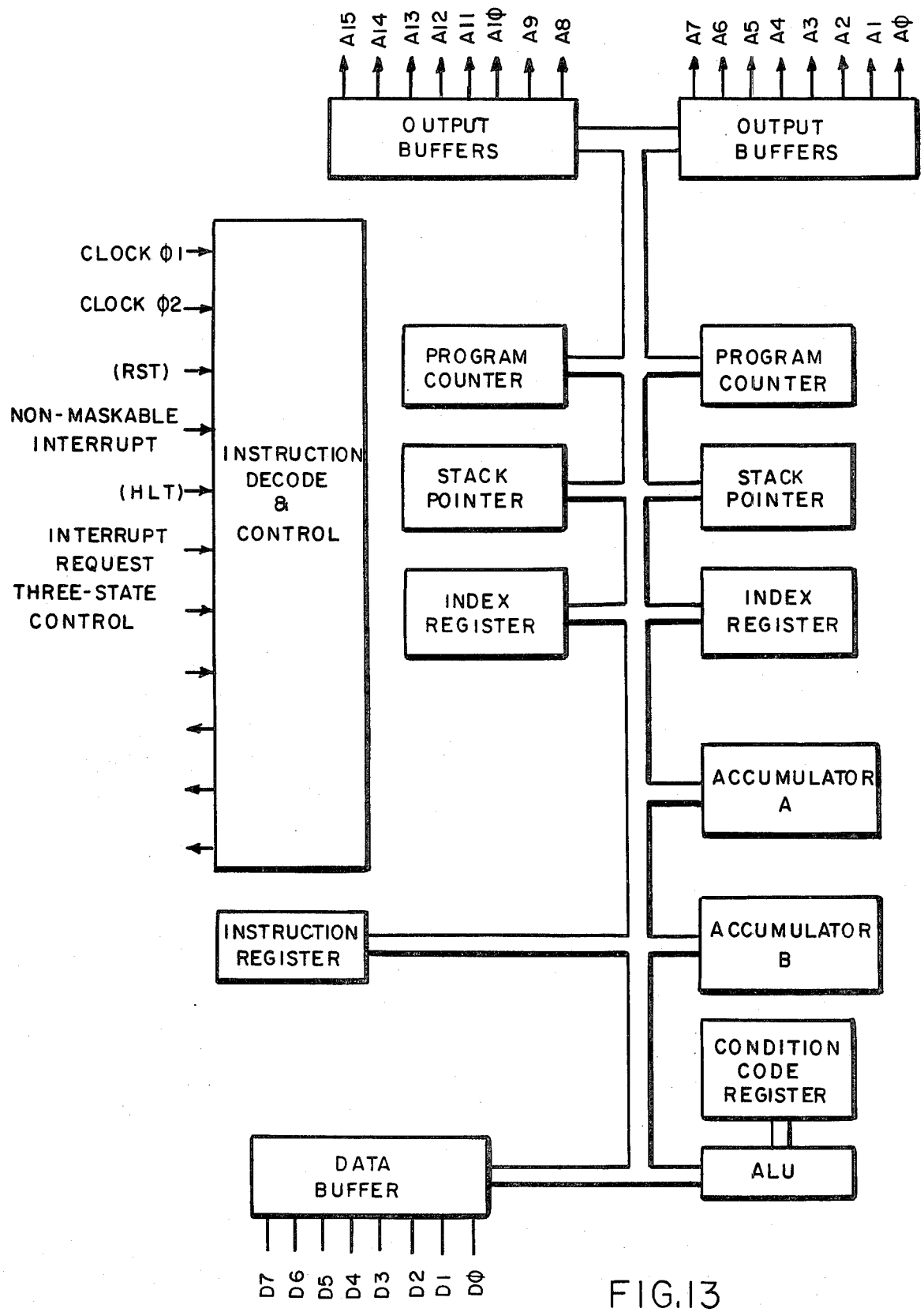
FIG. 13 depicts in block diagram form a particular embodiment of the microprocessor of the system of the invention.

The basic elements that make up the M6800 microprocessor are shown in block diagram form in FIG. 13. Other commercially available processors have similar architectures and can be used to implement the program architecture and algorithms described below. Some of the more important architectural features are listed below:

1. Eight-bit parallel processing.
2. Bi-directional data bus.
3. Sixteen-bit address bus allowing up to 65,536 bytes of addressing.
4. A 72-instruction repertoire.
5. Seven addressing modes: direct, relative, immediate, indexed, extended, implied and accumulator.
6. Interrupt structure using interrupt vectoring and separate non-maskable interrupt and interrupt request lines.
7. Six machine registers: Accumulator A, Accumulator B, Program Counter, Index Register, Stack Pointer and Condition Code Register.
8. Variable length stack resident in external RAM.

Figure 14:
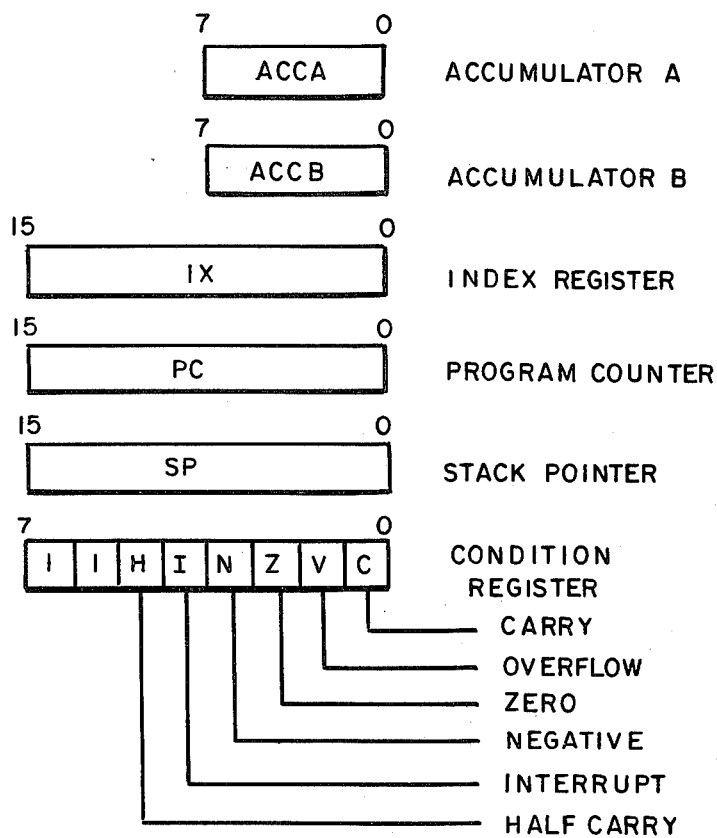
FIG. 14 depicts a model of the processor of FIG. 13.
Figure 15:
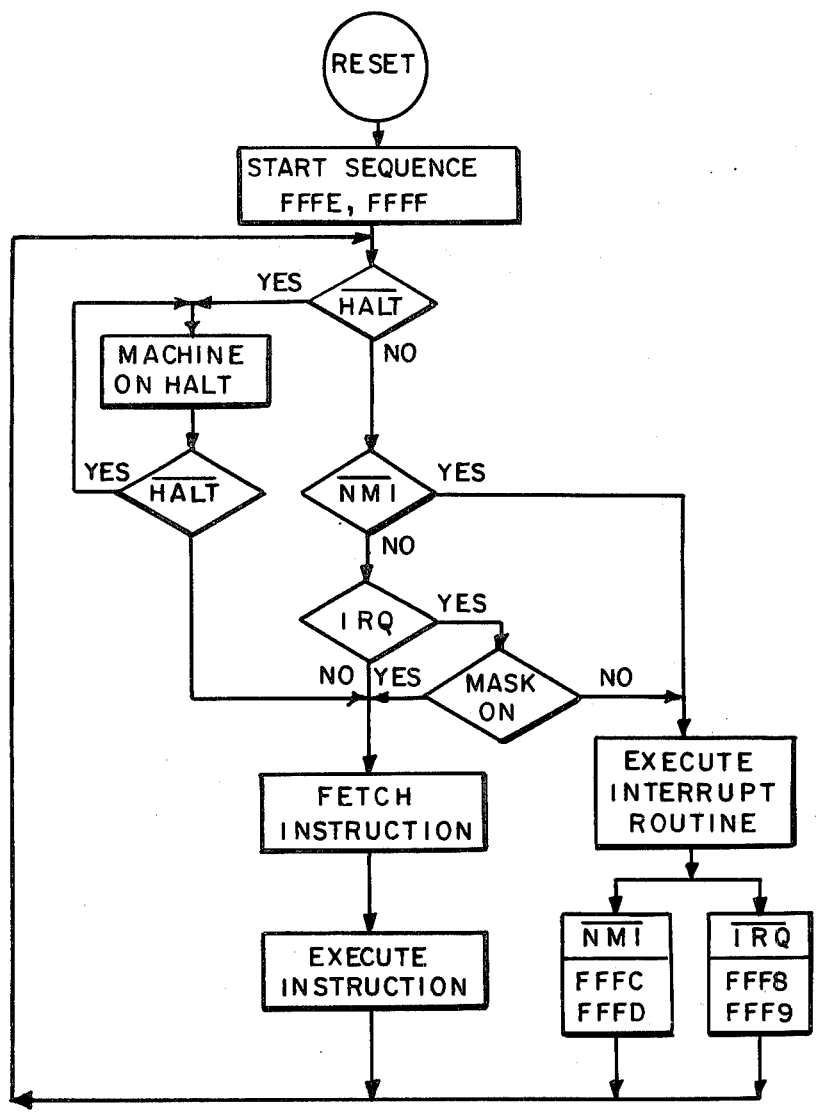
FIG. 15 depicts a flow chart showing the manner in which the microprocessor executes instructions.

A complete description of the M6800 is contained in Motorola specifications and support literature identified as "M6800 Microprocessor Programming Manual", Second Edition, and "M6800 Systems Reference and Data Sheets", Motorola Semiconductor Products, Inc., Phoenix, Arizona, 1975. In accordance with the use thereof in the embodiment of the invention discussed herein the processor is modelled as shown in FIG. 14. The manner in which the microprocessor executes instructions in the presence of hardware commands (Reset, Halt, NMI and IRQ) is shown in the flowchart of FIG. 15. The execution of the program instruction stored in the system ROM 53 is performed using the appropriate registers of FIG. 15 to manipulate and test the data stored in the system RAM 52. Two basic program types are used in this system: (1) Interrupt programs to place the data from the tool bit waveforms into RAM 52 via the A/D converter 44, and (2) Main programs that process and display the stored data.

Figure 16:
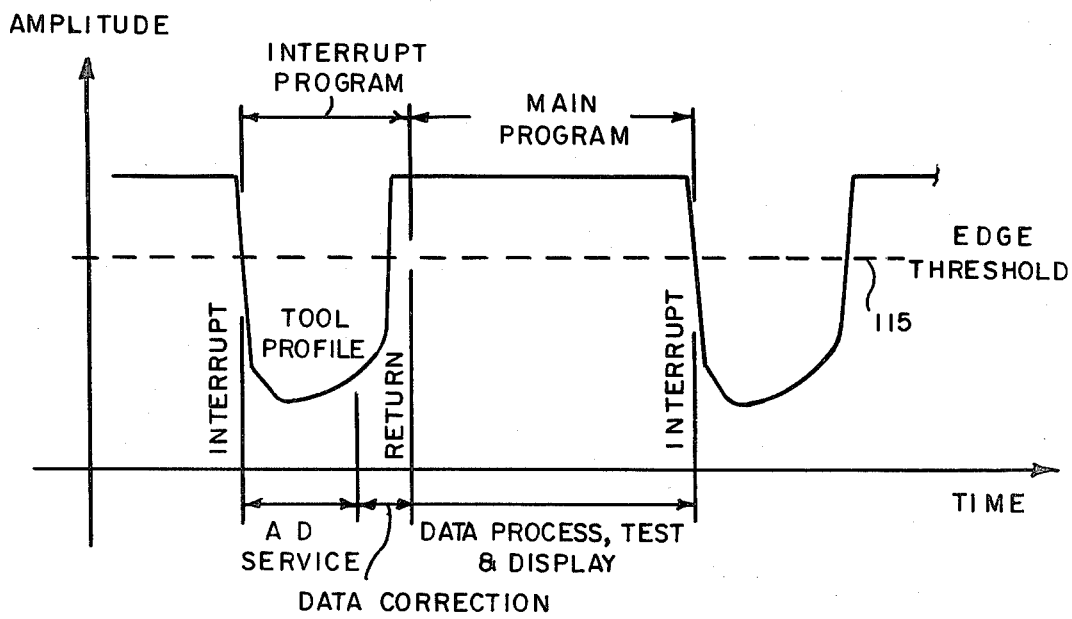
FIG. 16 depicts a typical waveform which is processed by the system of the invention.

The waveform that is being processed is shown in FIG. 16 (comparable to that shown in FIG. 3A) which depicts the amplitude thereof as a function of time. When the sensor voltage output to the A/D converter 44 reaches a preset value, shown as the edge threshold value at dashed line 115, the threshold detector 46 detects the existence of the incoming profile which is to be processed. The detector produces a system interrupt on the $\overline{\text{NMI}}$ line that commands the microprocessor to select an A/D service and data correction program stored in ROM 53. These programs are designed to sample the waveform, correct the data for sensor characteristics and place the corrected data into the system RAM 52. When the data has been taken and the Interrupt program is ended, the MPU then returns to the Main program, as selected on the Mode switch, and processes the data for wear characteristics. Tests are made to determine whether limits have been exceeded. Alarms and wear data are displayed on the system output devices. When the next incoming profile is sensed and an interrupt occurs, the microprocessor stores the information necessary to later resume wear processing in the system stack (part of RAM 52) and proceeds to the Interrupt program to take the data on the next tool bit.

Figure 17:
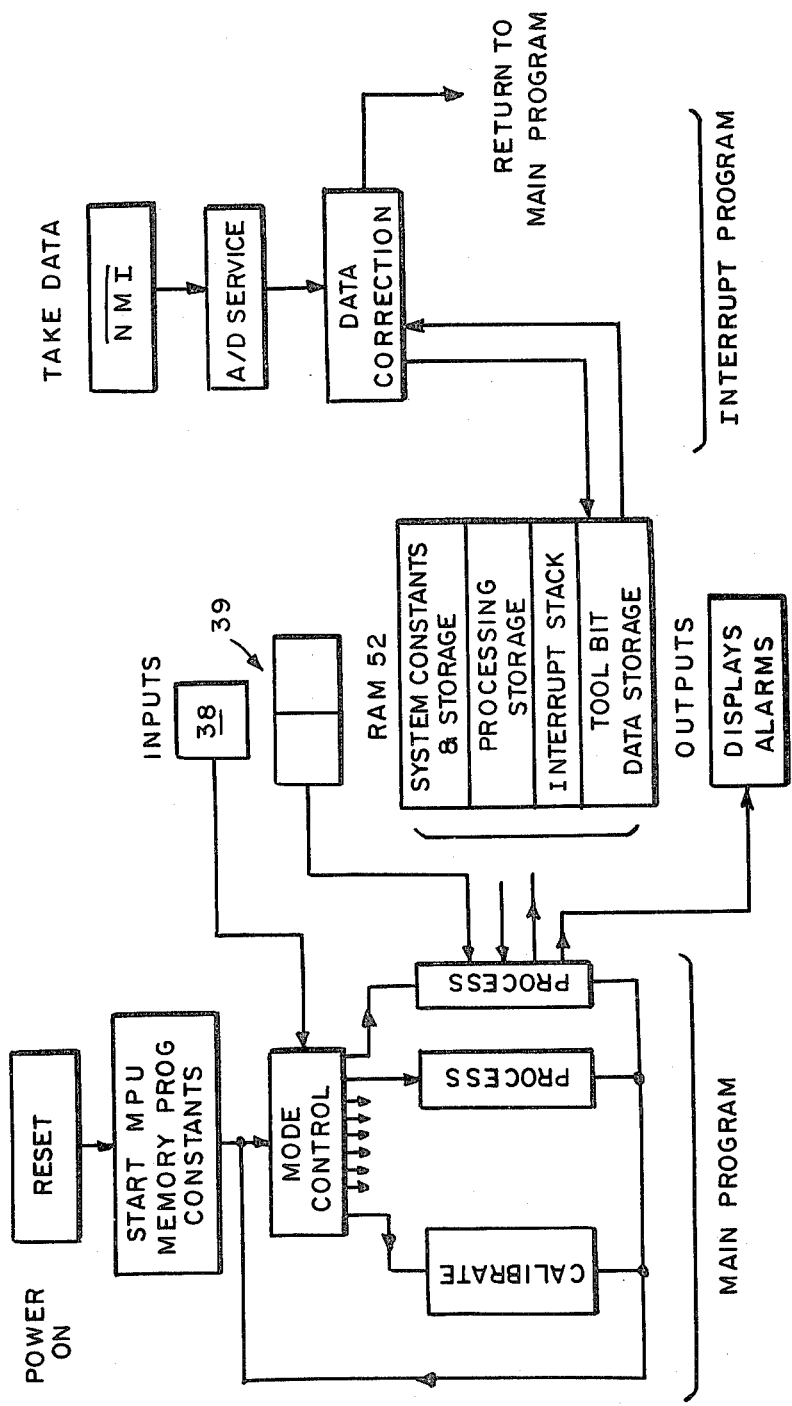
FIG. 17 depicts a block diagram showing the interaction of the Interrupt program and the Main programs of the system of the invention.

The interrelation of the Interrupt program and the Main programs in the system is shown in FIG. 17. Since the function of taking data has the highest system priority, it is done on a non-maskable interrupt basis. The Main program, which does processing that need not be done with great speed, operates on a lower priority basis using data supplied by the Interrupt program. Both program types share the use of the system memory.

The two basic functions of the Interrupt program, as shown in FIG. 17, are to service the A/D converter 44 to obtain the "raw" data and to correct it to account for the sensor and target characteristics. When the MPU has completed the correction process and stored the corrected data in memory, the MPU returns to Main program control for processing.

The Main program structure is also shown in FIG. 17. When the processing system is first turned on, the Main program initializes the MPU registers and places the information relevant to the tool type into the working areas of the system memory. The Mode switch 38 is then interrogated to select the processing programs to be used. The processing is then begun with updated data being supplied by the Interrupt program whenever a tool profile is sensed. User entry of data during processing can be done with the Data Entry switch 39 to provide thresholds or other constants to the program. Program output is provided with alarm lights, a two-digit numerical display and a meter for analog display.

The various programs used in the system are made up of short portions that are unique to the particular program and of subroutines that may be used in other programs and are called by the particular program. Such program structure allows writing a program that links the commonly used subroutines together rather than repeating the machine code necessary to implement the subroutine function in each program. Besides saving time in the programming of the system, using subroutines also saves memory and allows greater flexibility in program development.

Figure 18:
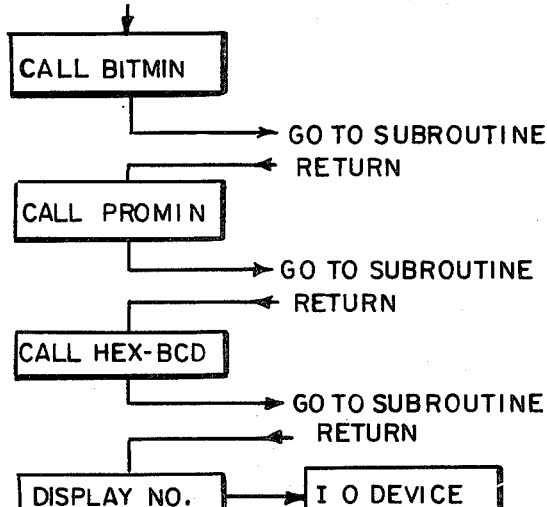
FIG. 18 depicts a typical processor program using several sub-routines.

An example of a typical processing program which uses several subroutines is given in FIG. 18. The subroutines shown therein operate on corrected tool data stored in the RAM 52 by the Interrupt program. In the program example shown, the highest leading edge of all the tool bits in the holder is determined and displayed on the numerical display output device.

When the program is started by the MPU, the first action is to call a subroutine designated "BITMIN" at location FCB0 in memory. The MPU goes to this location and executes the BITMIN program which finds the leading edge heights of each of the tool bits in a set, for example, of thirty-four tool bits of a milling-machine tool and stores them in RAM 52. When the subroutine is completed, the MPU returns to the process program and continues to the next instruction which calls for the subroutine designated "PROMIN". The MPU then jumps to the specified location at FCF0 and executes this subroutine which determines the highest one of the leading edge of all the tool heights. When completed, the MPU returns to the process program where it next finds an instruction calling for subroutine designated "HEX-BCD". The MPU again jumps to the subroutine requested at location FC60 and executes the HEX-BCD subroutine which converts the hexadecimally coded binary data on the highest leading edge tool height into binary coded decimal form. When the subroutine has been completed, the MPU returns to the process program to execute the next instructions which are unique to this particular program and call for the displaying of the highest leading edge tool height on the numerical display located at address 0402. After placing the data number in BCD form containing the height information into the display, the processing program is ready to continue to perform its next instructions.

Figure 19:
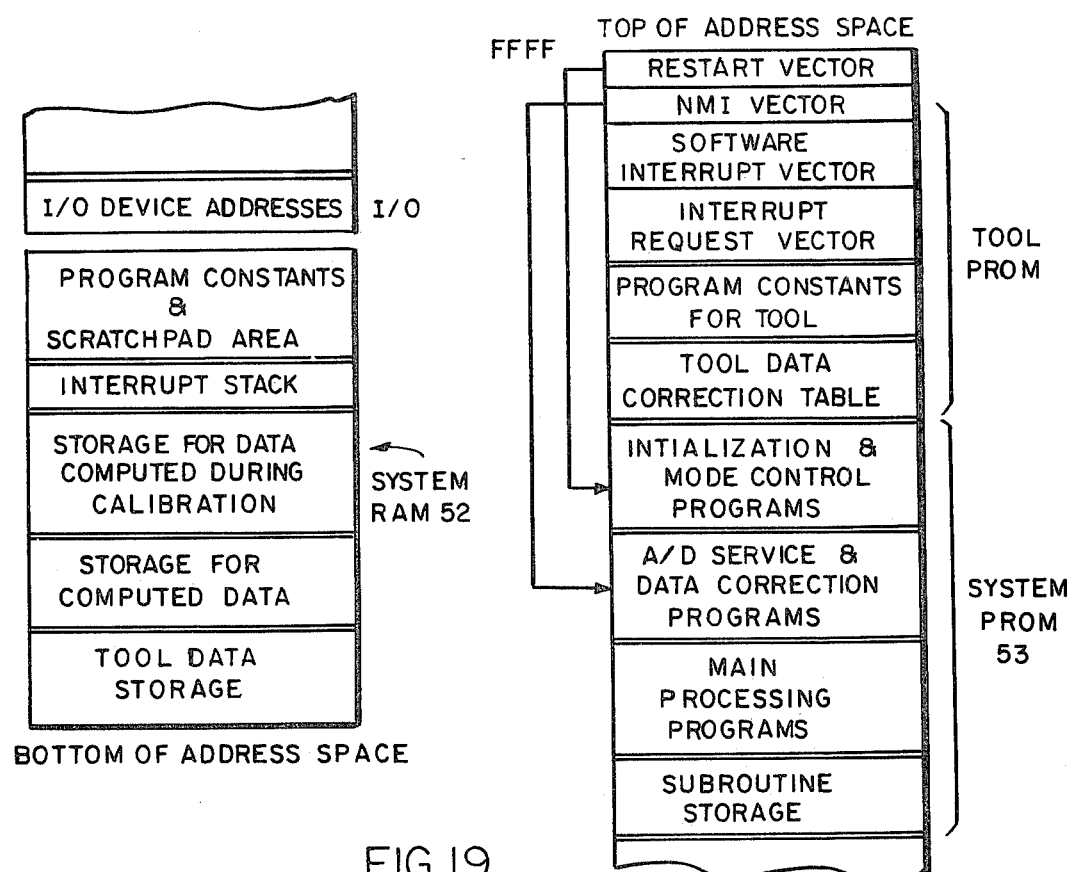
FIG. 19 depicts the typical memory allocations of the system of the invention.

Typical allocations in the memory are shown in FIG. 19. The subroutines used by the MPU and called for by the processing programs are stored in one portion of the ROM 53. The Main programs, consisting of programs that contain subroutine calls and instructions unique to the individual programs, are stored in another portion of ROM 53. The ROM also contains the Initialization program, used when power is turned on, and the A/D service and correction programs. The portion of ROM in the top address spaces is reserved for data correction tables and the storage of information unique to the particular tool type used. At the very top of memory are the vectors used by the MPU during reset and interrupts. These vectors are address pointers that tell the MPU where to go into the program when a reset or interrupt occurs. The ROM elements used to hold the subroutines and programs are physically separate from those used to hold the tool related information. This allows substitution of only one ROM element when the tool type is changed. By allocating more ROM memory to a given system, it is also possible to have several ROMs containing information on several tools which can be called for by the Mode switch when tool type is changed.

FIG. 19 also shows the allocation of space within the system RAM. The RAM section of memory is located in the lowest locations of the address space. This simplifies address decoding and allows expansion of the RAM capacity without major redesign of the system. The portion of RAM in the lowest addresses is reserved for the storage of tool data obtained by the Interrupt programs. The remainder of the RAM stores computed data from the Main programs, calibration data and further contains a working area in which the program constants and tool information are stored for access by the system programs. A portion of the RAM is also reserved for use as a stack area in which information is temporarily stored during program interrupts.

The I/O devices (i.e. A/D converter, displays, alarms, switches) are accessed by the MPU as if they were part of memory. They are called by referring to their address within the memory space. In a generalized processing system, they are located immediately above the RAM. Up to eight I/O devices may be accessed, even though only four addresses are used, by decoding whether a read or write operation is being performed.

Figure 20:
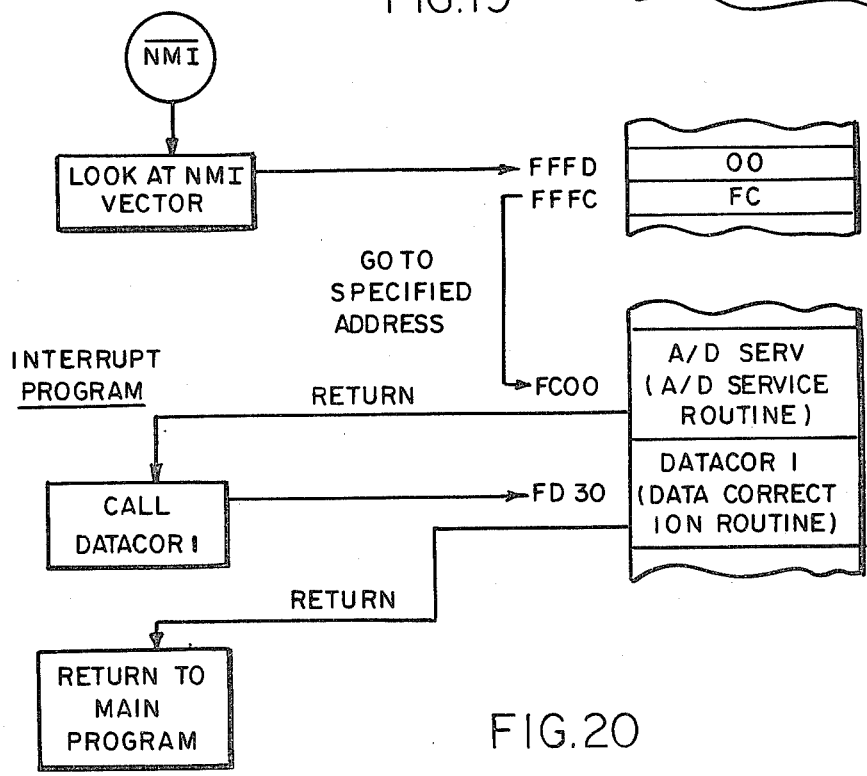

The Interrupt program is shown in FIG. 20 and is initiated by a non-maskable interrupt created when the input waveform to the processing system is sensed. When the MPU senses the interrupt, as in the flowchart of FIG. 20, it looks at the location in memory containing the NMI vector. The vector tells the MPU where in the ROM to find the first instruction of the Interrupt program, in this case, an instruction to start the A/D service subroutine. When the A/D service subroutine is completed, and the data stored, the MPU returns to the Interrupt program, which contains the instruction to call for the data correction subroutine designated "DATACORI" a location FD30 of ROM 53. The MPU goes to this routine and corrects the data stored in memory for sensor and target characteristics. When finished, the MPU returns to the Interrupt program, which thereupon signifies that the program is complete and commands the MPU to return to whatever it was performing in the Main program.

Figure 21:
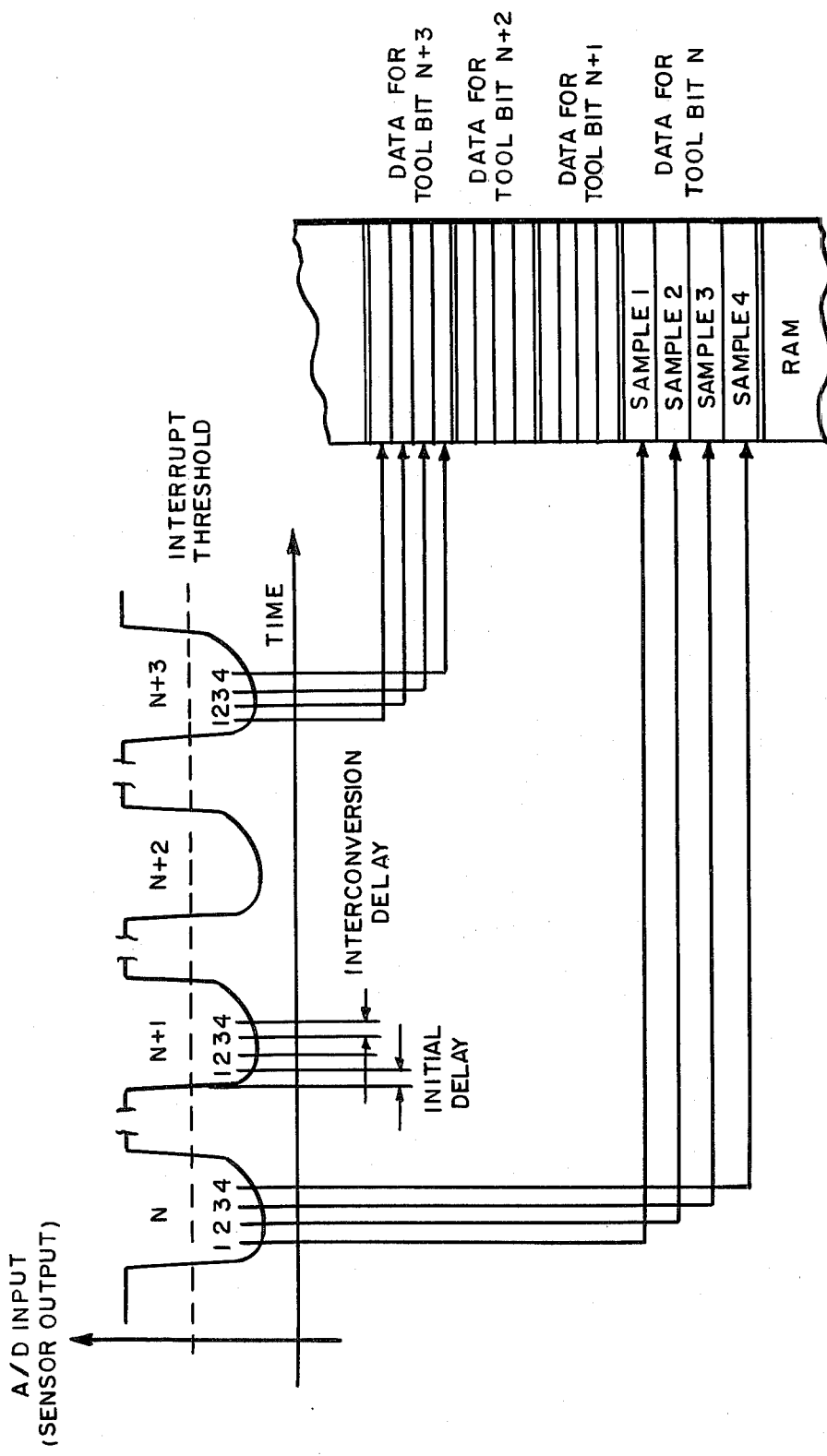

The function of the A/D service subroutine as discussed with reference to FIG. 21 is to sample the sensor waveform at program controlled times and to place the resulting data into the RAM for processing. When the system is initialized, constants that control the number of samples, the initial delay for the first sample and the time between the samples are preset in the working area of RAM. These are referred to by the subroutine.

The initial and interconversion delay times are controlled by timing loops within the subroutine. For a typical program, for example, the delay times can be programmed in increments of 12 micronseconds up to a maximum of about 3 milliseconds for each delay.

The samples taken are stored in the RAM 52 in adjacent blocks of data, each block containing the data samples on a given tool bit. The storage of the data into adjacent blocks with no wasted addresses in memory is done automatically by the subroutine by using the information on the number of samples to be taken and the number of tool bits that were stored in the working area of RAM by the Initialization program.

When the last data sample has been taken, the subroutine returns control to the Interrupt program. For normal operation of the system, where data correction must be done before processing, the next instruction in the Interrupt program calls a data correction subroutine.

In connection with the latter subroutine, as mentioned above, certain errors can arise because of the sensor and tool bit characteristics with errors, once characterized, can be corrected in several ways.

If the error function can be expressed in the form of an equation, the correction can be computed by an algorithm in the MPU. A difficulty with such method is that it may require multiplication and division operations or the use of transcendental functions. The instruction sets for most microprocessors which are presently available normally do not include these capabilities and, therefore, new programs would have to be devised to accomplish these functions. While such programs could be devised by those in the art for use in the invention, they would require a prohibitive time overhead for processing and the use of such a correction method would not be the most effective during system interrupts.

On the other hand, error functions expressible in the form of tables or graphs can be readily used by microprocessors since the error information can be entered in tabular form (i.e. "look up" tables) in memory. The error can then be looked up by the correction program and subtracted from the data taken by the system.

An advantage of the latter technique for error correction is that, in principle, the microprocessor can create the correction table on the basis of what the sensor output would ideally be. If the MPU knows what the waveform should be if the sensor were perfect, it can take the data it actually sees on a new tool bit and subtract it from the ideal waveform. The difference, or error, would then be stored in a table in memory for later use in error correction.

Still another alternative can be used wherein the data is corrected by the use of a table generated by the user, not by the processing system.

Figure 22:
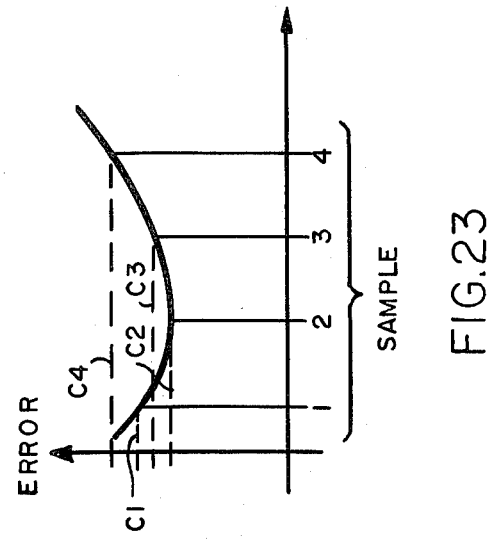

Such a system, for example, corrects the data obtained by the A/D service subroutine with the subroutine shown in FIG. 22 for the four samples per tool bit example discussed above. The error characteristics of the tool and sensor are entered into a portion of the ROM 53 using data numbers generated from a graph of the error function in the expected region of sensor operation, a typical such graph being shown in FIG. 23. The ROM element in which the error characteristics are entered can either be changed for different tool types or several ROM elements can be provided in the system which can be separately called for using the Mode switch.

As seen in FIG. 22, the subroutine starts by fetching the data to be corrected from the RAM 52. The error for this data sample is then obtained from the appropriate correction table in ROM 53 and the two numbers are subtracted. The corrected data is then returned to the same location in RAM 52 from which the uncorrected data was taken. The subroutine then moves to the next data location and corrects it, continuing until the complete block of data for the given tool bit has been corrected. The subroutine then returns to the Interrupt program. The next instruction in the Interrupt program returns control to the Main processing program, where the data is processed for wear characteristics.

Figure 23:
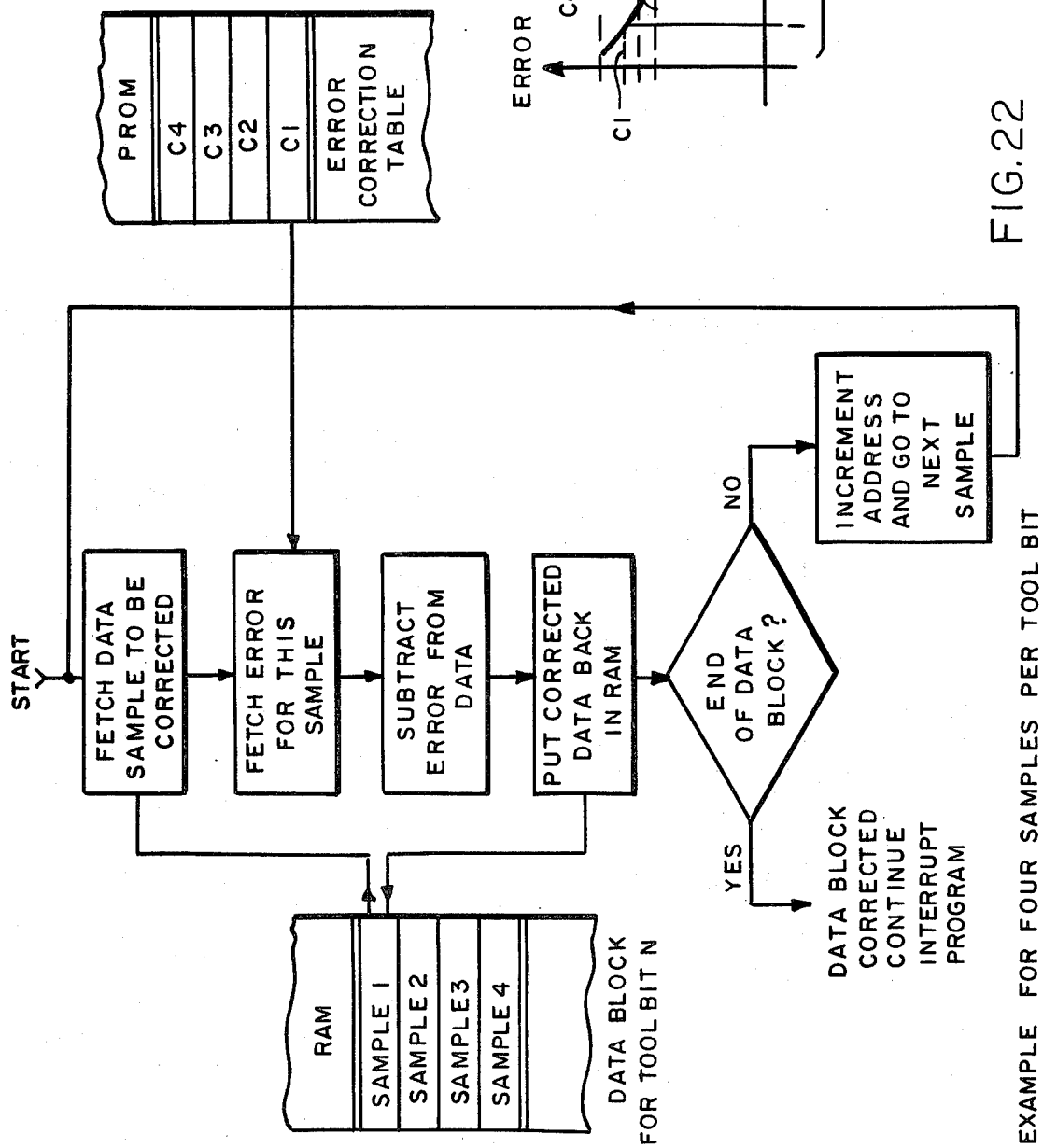
FIG. 23 depicts in graphical form the error as a portion of the sampled measurement taken on a typical tool bit.

The error functions shown in FIG. 23 are slightly dependent on the distance from the sensor to the tool bits. This residual error will change slightly as the tool bits wear and appear farther from the sensor. The dominant portion of the error caused by the edge effects has been removed, however, by the error-function of FIG. 23. Should increased accuracy be necessary in certain applications, for example, several tables can be used with the selection of the correction table being made on the basis of the apparent height and the sample time of the data which is being sensed. Whether such a secondary correction is necessary depends on the wear mechanisms of the tool used and the accuracy needed to resolve them.

Some of the typical subroutines that can be called in the Main program are shown below in Table I.

TABLE I

| Subroutine Name | Words of Memory Used | Subroutine Function |
|---|---|---|
| A/D SERV | 63 | Samples sensor waveform and stores data in memory. Controls sampling delays. |
| DATACOR1 | 37 | Corrects data blocks in memory for sensor target errors using "look up" table in ROM. |
| BITMIN | 61 | Finds minimum data number in each tool bit data block. |
| PROMIN | 26 | Finds minimum data number in set of minimums found by BITMIN. |
| PROMAX | 26 | Finds maximum data number in set of minimums found by BITMIN. |
| RECON | 24 | Reconstructs waveform from corrected or uncorrected output using D/A. |
| BCD-HEX | 31 | Converts binary coded decimal data to hexadecimal code. |
| HEX-BCD | 43 | Converts hexadecimal coded data to binary coded decimal. |
| INIT | 27 | Initizlizes working areas of memory after power to system is turned on. |
| ALARM | 10 | Tests alarm status and displays alarms. |
| CALSUB | 31 | Subtracts data taken during calibration from data during wear processing and compares with user specified thresholds Sets alarm status. |
| BLKAVG | 35 | Finds average of data in each tool bit data block (uses DIV as a subroutine). |
| AVGMAX | 26 | Finds maximum of averages obtained by BLKAVG. |
| AVGMIN | 26 | Finds minimum of averages obtained by BLKAVG. |
| SUMAVG | 30 | Finds sum of averages found by BLKAVG. |
| CALMOV | 13 | Moves data obtained during calibration into area of memory reserved for calibration data. |
| MODE | 59 | Interrogates mode switch and vectors Main program to appropriate subprogram. |
| DIV | 69 | Divides two 16-bit numbers giving a 16-bit result in Accumulators A and B. |

The function of each is described as well as the exemplary amount of memory space each requires in the system ROM 53. Processing for wear or system diagnostics can be performed by linking such subroutines together with specific instructions for I/O control in the Main program. The number of ways these programs can be used is extensive and two typical examples of general processing algorithms are discussed below. One algorithm is for calibration and the other for wear measurement. For these examples, processing is assumed to be done on four samples for each of 34 tool bits as in a 9" face milling tool.

The calibration algorithm is used when the new tool has been installed on the machine tool, the first use of the system being to "memorize" the tool characteristics before cutting begins. The Mode switch is set to Calibrate and the processor utilizes the calibration algorithm in Main program after the system is initialized. The machine tool is started and data is taken and corrected by the Interrupt program while the calibration algorithm in the Main program is operating on a time available basis.

The calibration algorithm is shown in flow chart form in FIGS. 24 and 25 and consists of subroutines that find various properties of the sampled data, tests them and stores them in a region of the RAM 52 reserved for calibration data. Thus, as shown in FIG. 24, the subroutines find the leading edge heights for each tool bit, the highest leading edge for the set of 34 tool bits, the lowest leading edge for the set of 34 tool bits. The subroutines then test the radial runout of the installed tools and test to see whether the highest leading edge is too close or too far from the sensor. Further, as shown in FIG. 25, the subroutines find the average leading edge height for all 34 tool bits, the average flank dimension of each tool bit, the highest average flank dimension for all 34 tool bits, the lowest average flank dimension for all 34 tool bits, and the sum of the average flank dimension for all 34 tool bits. The above values are all stored in a selected portion of the memory for later reference.

Further, during calibration, the system can perform tests to ensure that the system is properly aligned and that the tool has been properly fixtured. These tests are done readily in the system as compared with the difficulty in performing such tests in analog type systems.

Figure 27:
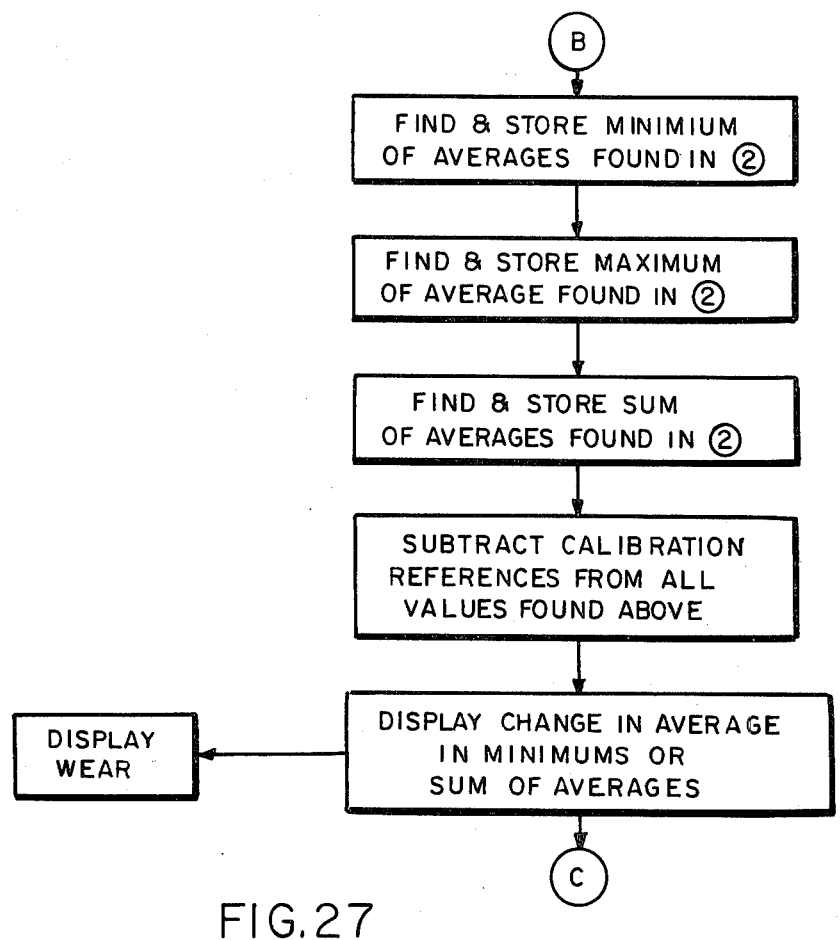
Figure 28:
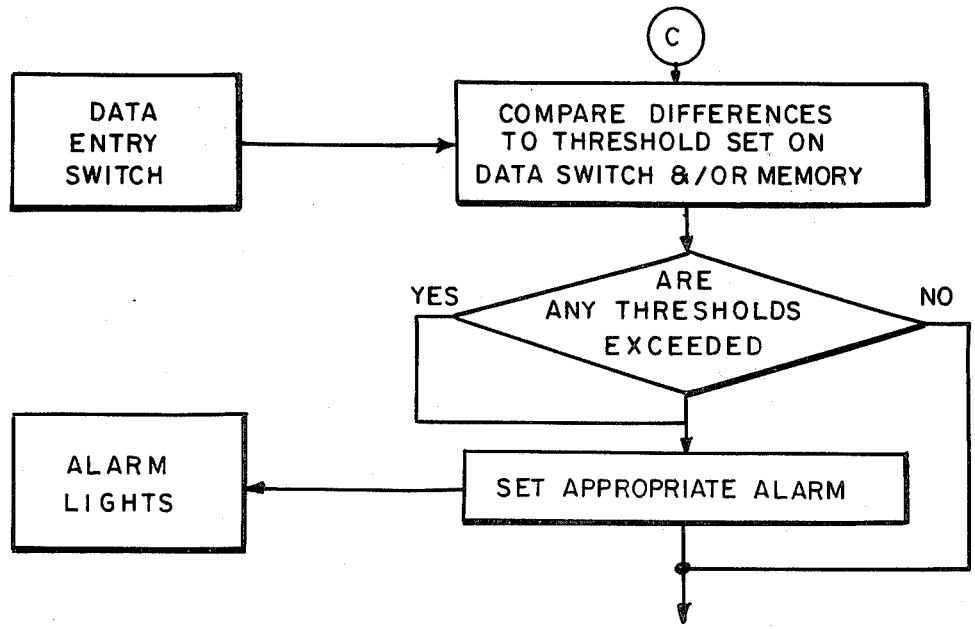

After calibration, the Mode switch can be activated to select a measurement algorithm from the Main program, as shown by the typical flow chart representation thereof in FIGS. 26, 27 and 28. As can be seen many of the subroutines therein are used in the previously discussed calibration operation for finding the tool parameters during actual operation of the system. Such tool parameters are compared to the values found during calibration. Accordingly, as shown in FIGS. 26 and 27 the highest, lowest and average leading edges and the highest and lowest average and sum of averages of flank dimensions of each tool bit are found and the differences between such values and the comparable values found during calibration are determined, such differences being displayed as a measure of leading edge or flank wear. As seen in FIG. 28 such differences are compared with preset wear limits to set appropriate alarms when such limits are exceeded.

Thus, the system has the capability of finding any desired wear mode that can be processed using peak detection, finding mean values or by averaging. The flexibility in the way data can be processed and displayed provides significant advantages over analog processing methods.

The processing overhead, i.e., the percentage of operating time the system is actively processing, is dependent on how the system is used as a measurement device. In the specific context discussed above, for example, if the system is constantly monitoring the exemplary milling tool described therein, and uses the particular processor described therein, the percentage of time in the Interrupt program is approximately equal to the duty cycle of the tool bit. For a 9" face milling tool, for example, it would be in Interrupt program about 31% of the time. The rest of the time, the system would be in Main program, processing wear or whatever other processing the Mode switch provides for. For most wear processing algorithms, the time needed to process the data is longer than the time between acquisition of data from the successive tool bits. This condition is acceptable since wear information is not readily usable at times other than when the tool has completed the cut on the workpiece. Since the time to complete a cut on the workpiece is measured in seconds, the wear information can also take a similar time to be processed. Most algorithms will take considerably less time, therefore, the processor can be used to perform other tasks if desired. In other applications, the processing overhead depends on the particular tool being monitored and the particular processor which is used. In any event, in many cases the processing circuitry can be used to monitor more than one tool if it is appropriately synchronized for operation therewith.

If the measurement system is interfaced with a machine tool's control computer using an interrupt to call for wear data processing and if the interrupt used is of lower priority than the one used to initiate the Interrupt program in the measurement system (for example, by using the IRQ line in the system), the minimum wear processing overhead is about 31%. The total overhead necessary to get the wear information will then be greater than 31%, depending on how often the information is requested by the machine tool computer.

If the interrupt from the machine tool computer is made to have higher priority than that used to acquire the tool bit data samples, the processing overhead for the wear measurement can be significantly lowered. The exact overhead, however, will depend on the type of interrupt architecture used. The minimum value will be constrained, however, by the interrupt rate and the time for one complete revolution of the mill head since processing depends on data ensembles obtained over the complete set of tool bits.

The ability to interface using interrupts with a machine tool or central computer is one of the significant advantages of the microprocessor based measurement system of the invention. The ability to manage and control the taking of data is an advantage that analog type tool wear measurement systems cannot achieve.

While the above embodiments of the invention have discussed the use thereof with a milling tool it is clear that the system is readily adaptable for use with any types of tool wherein the cutting surface (or surfaces) thereof is accessible to a locally mounted sensor. Further, the system is not limited to the particular processor discussed above as other processors can be used therefor.

In summary, the invention provides a direct, on-line, real-time tool wear monitoring system which is broadly applicable to many different tool types, the operation of which is extremely flexible since it requires substantially little or no mechanical modifications to the tools being monitored. Its overall cost is comparable to tool wear measuring systems presently available, while providing the advantages of a system which is self-calibrating and is furthermore self-correcting in that the system can be arranged to provide an alarm, for example, if the tool bits in a multiple bit tool have been improperly installed or if the sensor has been incorrectly located with reference to the tool cutting surfaces which are being monitored.

The invention is not to be construed as limited to the specific embodiments disclosed above except as defined by the claims.

What is claimed is:
1. A system for determining the wear characteristics of at least one cutting tool comprising
  at least one sensing means for producing an output signal representing the cutting profile characteristics of said at least one cutting tool as said tool passes adjacent thereto;
  data processing means responsive to said at least one sensing means output signal for storing information concerning said cutting profile characteristics when said cutting tool is initially installed for use and for obtaining up-dated information concerning said cutting profile characteristics during subsequent use of said cutting tool;
  means for comparing said initial stored profile characteristics information with said up-dated profile characteristics information to provide output information concerning the wear characteristics of said at least one cutting tool.
2. A system in accordance with claim 1 and further including display means responsive to said output information for providing said information in a sense-responsive form for an operator of said system.
3. A system in accordance with claim 2 wherein said display means comprises a visual display means.
4. A system in accordance with claim 2 wherein said display means comprises an audible display means.

5. A system in accordance with claim 4 wherein said audible display means produces an audible alarm signal when said output information indicates that the wear characteristics of said at least one cutting tool exceeds preselected limits.

6. A system in accordance with claim 1 wherein said sensing means provides an analog output signal and said data processing means is a digital processing means and includes means for converting said analog output signal to a digital output signal for processing by said digital processing means.

7. A system in accordance with claim 6 wherein said digital data processing means includes
- a memory unit capable of storing said initial profile characteristics information and said updated profile characteristics information,
- a microprocessor unit for controlling the storage of said initial and said updated profile characteristics information in said memory unit and the access to said stored information, for controlling the comparison of said initial and said updated profile characteristics information and for controlling the supplying of said output information concerning said wear characteristics.

8. A system in accordance with claim 7 wherein said memory unit comprises a random-access-memory for storing said profile characteristics information initially obtained and subsequently offered during use and a read-only-memory for storing program information for use by said microprocessor unit.

9. A system in accordance with claim 1 and further including means for interrupting the operation of said data processing means when information concerning a cutting tool profile is produced from said sensing means and for permitting said data processing means to resume its operation when said cutting tool profile information has been stored.

10. A system in accordance with claim 1 and further including interface means for providing an interconnection of said system with one or more systems external thereto.

11. A system in accordance with claim 10 wherein said interface means includes means for interrupting the operation of said data processing means in response to an external data processor means to provide for communication between said data processing means and said external data processor means.

12. A system in accordance with claim 1 and further including means for correcting errors which arise because of sensor and tool bit characteristics.

13. A system in accordance with claim 12 wherein said error correcting means includes
- means for storing error information in accordance with a predetermined error equation associated with a selected cutting tool type; and
- means for comparing said error information with said updated cutting tool profile information to produce corrected cutting tool profile information.

14. A system in accordance with claim 12 wherein said error correcting means includes
- means for comparing the initial cutting tool profiles of each of said at least one cutting tool with a predetermined ideal cutting tool profile; and
- means for storing information representing differences therebetween, said difference information being available for use in correcting said updated cutting tool profile information.

15. A system in accordance with claim 12 wherein said error correcting means includes
- means for storing predetermined error information concerning said at least one cutting tool profile, said predetermined error information being available for use in correcting said updated cutting tool profile information received from said sensing means.

* * * * *